United States Patent [19]

Ceriani et al.

[11] Patent Number: 5,455,031

[45] Date of Patent: Oct. 3, 1995

[54] POLYPEPTIDE WITH 46 KDALTON HMFG DIFFERENTIATION ANTIGEN BINDING SPECIFICITY, COMPOSITION, KIT & DIAGNOSTIC METHOD

[75] Inventors: Roberto L. Ceriani; Jerry A. Peterson, both of Lafayette; David J. Larocca, San Leandro, all of Calif.

[73] Assignee: Cancer Research Fund of Contra Costa, Walnut Creek, Calif.

[21] Appl. No.: 607,538

[22] Filed: Nov. 1, 1990

[51] Int. Cl.⁶ .......................... C07K 13/00; A61K 39/00; C12Q 1/00
[52] U.S. Cl. .................... 424/185.1; 424/184.1; 435/7.1; 530/350
[58] Field of Search ................ 424/88, 184.1, 424/185.1; 530/350; 435/7.1

[56] References Cited

U.S. PATENT DOCUMENTS

| | | | |
|---|---|---|---|
| 4,348,384 | 9/1982 | Horikoshi et al. | 424/450 |
| 4,857,635 | 8/1989 | Zimmerman et al. | 530/383 |

OTHER PUBLICATIONS

Kane et al Proc Natl. Acad Sci vol. 83 pp. 6800–6804.
Nakagawa et al B.B.R.C. vol. 127(1) pp. 8–14 1985.
Stubbs, J. D., et al, "cDNA cloning of a mouse mammary epithelial cell surface protein reveals the existence of epidermal growth factor–like domains linked to factor VIII–like sequences" P.N.A.S. (USA) 87:8417–8421 (1990).
Ceriani, R. L., et al, "Experimental Immunotherapy of Human Breast Carcinomas Implanted in Nude Mice with a Mixture of MOnoclonal Antibodies against Human Milk Fat Globule Components" Cancer Research 47:532–540 (1987).
Ceriani, R. L., et al, "Characterization of Cell Surface Antigens of Human Mannary Epithelial Cells with Monoclonal Antibodies Prepared Against Human Milk Fat Globule", S.C.G. vol. 9, No. 4:415–427 (1988).

Ceriani, R. L., et al, "Breast Epithelial Antigens in the Circulsation of Breast Cancer Patients", Sec.Ed:223–241 (1991).
Ceriani, R. L., et al, "Experimental Therapy of Human Breast Tumors with $^{131}$I–labeled Monoclonal Antibodies Prepared against the Human Milk Fat Blobule", Cancer Research 48:4664–4672 (1988).
Peterson, J. A., et al, "Biochemical and Histological Characterization of Antigens Preferentially Expressed on the Surface and Cytoplasm of Breast Carcinoma Cells Identified by Monoclonal Antibodies Against the Human Milk Fat Globule", Hybridoma vol. 19, No. 3: (199), pp. 221–235.
Ceriani, R. L., et al, "Circulating human mannary epithelial antigens in breat cancer", P.N.A.S. (USA) 79:5420–5424 (1982).
Salinas, F. A., et al, "Significance of Breast Carcinoma–associated Antigens as a Monitor of Tumor Burden: Characterization by Monoclonal Antibodies", Cancer Research 47:907–913 (1987).
Ceriani, R. L., et al, "Surface differentiation antigens of human mammary epithelial cells carried on the human milk fat globule", P.N.A.S. (USA) vol. 74, No. 2:582–586 (1977).
Sasaki, Masao, et al, "Quantitation of Human Mammary Epithelial Antigens in Cells Cultured from Normal and Cancerous Breast Tissues", InVitro vol. 17, No. 2:0150–0158 (1981).

*Primary Examiner*—Mindy B. Fleisher
*Attorney, Agent, or Firm*—Ratner & Prestia

[57] ABSTRACT

A polypeptide has the antibody binding activity of the 46K dalton HMFG differentiation antigen and/or homology to at least one of the light chains of clotting factors V and VIII and is also provided as a fusion protein with a second antigenic polypeptide. An antibody has affinity for the polypeptide of the invention or a functional fragment thereof. in vivo and in vitro methods for therapy vaccination and detecting the presence of the polypeptide, the antibody, the DNA and RNA of the invention are provided. DNA and RNA sequences encode the polypeptide of the invention or fragments thereof and immunoassay kits comprise the antibodies and/or polypeptides of the invention.

6 Claims, 1 Drawing Sheet

POLYPEPTIDE WITH 46 KDALTON HMFG DIFFERENTIATION ANTIGEN BINDING SPECIFICITY, COMPOSITION, KIT & DIAGNOSTIC METHOD

TECHNICAL FIELD

This invention relates to a polypeptide having the antibody binding specificity of the 46 kDalton HMFG differentiation antigen, a polynucleotide, and a polyribonucleotide encoding it, anti-polypeptide antibodies, methods of detecting the polypeptide and DNA and RNA encoding it, a method of imaging cells expressing the polypeptide, a method of detecting the presence of the polypeptide in a biological fluid by binding the antibody to the polypeptide, in vivo and ex vivo methods of delivering a therapeutic agent to a target cell expressing the polypeptide, a fusion protein of the polypeptide and at least one other polypeptide, labeled polynucleotides and polyribonucleotides encoding the polypeptide and a complementary DNA sequence, method of detecting RNA and DNA by hybridization with labeled probes, a method of vaccination with the polypeptide, and method of treating breast cancer with an anti-sense DNA.

BACKGROUND ART

The human milk fat globule (HMFG) has been used extensively as a source of antigenic material for the preparation of both polyclonal and monoclonal antibodies that have found widespread use in the diagnosis of breast cancer, as well as in the study of the breast epithelial cell surface and the processing of its antigenic components.

Polyclonal antiserum was originally prepared, that after appropriate absorptions with non-breast tissue was found to identify surface antigens of human mammary epithelial cells (HME-Ags). This antiserum (anti-HME) had a high specificity for normal breast epithelial cells and breast carcinomas. It identified mainly three components of the human milk fat globule which had molecular weights of 150 kDa, 70 kDa, and 46 kDa, respectively.

Monoclonal antibodies were first made against the HMFG in 1980. These antibodies were applied to identify a hitherto unknown component of the breast epithelial cell surface, a large molecular weight mucin-like glycoprotein, that was named non-penetrating glycoprotein (NPGP). This latter component appears to be extremely antigenic in the mouse. The vast majority of monoclonal antibodies prepared against HMFG as well as breast tumors have been found to lave specificity against different epitopes of this mucin complex. Less frequently, monoclonal antibodies have been prepared against the 70 kDa and 46 kDa components of the HMFG.

The reason for the high immunogenicity of NPGP has recently been elucidated by the characterization of cDNA clones selected from a kgt11 breast cell library using both polyclonal and monoclonal antibodies against the mucin. These cDNA clones consist of large arrays of highly conserved 60 bp tandem repeats. The resulting 20 amino acid repeat contains epitopes for several anti-mucin antibodies.

The repeat is apparently unstable at the genomic level. This may account for the observed polymorphism seen at the gene, RNA and protein levels for this high molecular weight mucin. An initial report on cDNA cloning of the mucin product suggested that the core protein had a molecular weight of about 68 kDa. However, the mRNA was found to be large enough to code for proteins from about 170 kDa to 230 kDa. More recently, using milder deglycosylation methods, a core protein was identified having a molecular weight of about 200 kDa.

Attention has also been devoted to the study and use of the NPGP mucin complex, largely as a result of its high immunogenicity. Thus, a large number of monoclonal antibodies were prepared against it. However, the smaller components of HMFG also appear to be important molecules on the surface of breast epithelial cells. They have a breast specificity as demonstrated by the anti-HME antibodies.

The 46 kDa and 70 kDa HME antigens are found in serum of breast cancer patients and thus can be used as markers for breast cancer in serum assays. In addition, the 70 kDa component has been found to co-purify with the intact mucin complex and has been reported to be associated with the NPGP mucin complex by means of disulfide bonds, making it a possible linker protein of this surface mucin complex.

Few monoclonal antibodies have been prepared against the smaller components of the system. The mucin molecule is apparently more antigenic because of its internally repeated structure. The 46 kDa component of HMFG has been found in the serum of breast cancer patients. Using monoclonal antibodies against the 46 kDa antigen, circulating immune complexes were found in breast cancer patients and an increase in the circulating 46 kDa antigen was found to be associated with increased tumor burden. The structure of the mucin glycoprotein has recently been determined by cDNA cloning and a partial sequence has been reported for the 70 kDa antigen.

Very little, however, is known about the structure of the 46 kDa antigen and its function, along with the other membrane components, in the normal epithelial cell membrane, milk formation, and breast tumorigenesis. Up to the present time neither the sequences of the about 46 kDalton polypeptide component nor the DNA and RNA encoding it were known.

DISCLOSURE OF THE INVENTION

This invention relates to a polypeptide having the antibody binding specificity of the about 46 kDa HMFG differentiation antigen and/or homology to at least one of the light chains of clotting factors V and VIII.

This invention also relates to a fusion protein, comprising
 a polypeptide having the antibody binding specificity of the about 46 kDalton HMFG differentiation antigen and/or homology to at least one of the light chains of clotting factors V and VIII; and
 a second antigenic polypeptide bound thereto.

Still part of this invention is an antibody having specificity for a polypeptide having the antibody binding activity of the about 46 kDalton HMFG differentiation antigen and/or homology to at least one of the light chains of clotting factors V and VIII or a functional fragment thereof.

Also provided herein is a method of detecting the presence of a polypeptide having the antibody binding activity of the about 46 kDalton HMFG differentiation antigen and/or homology to at least one of the light chains of clotting factors V and VIII or a functional fragment thereof in a biological sample, comprising providing a biological sample suspected of comprising the polypeptide;

adding thereto a polypeptide binding effective amount of an antibody having specificity for a polypeptide having the antibody binding specificity of the about 46 kDalton HMFG differentiation antigen and/or homology to at least one of the light chains of clotting factors V and VIII or a functional fragment thereof under conditions effective to form an antibody-polypeptide complex; and determining the presence of any complex formed therebetween.

Also part of this invention is a method of determining the presence of epithelial cells in a biological sample, which comprises providing a biological sample suspected of comprising cells of epithelial origin carrying a polypeptide having the antibody binding activity of the about 46 kDalton HMFG differentiation antigen and/or homology to at least one of the light chains of clotting factors V and VIII or a functional fragment thereof;

adding thereto a polypeptide binding effective amount of an antibody having specificity for the polypeptide described above, under conditions effective to form an antibody-cell polypeptide complex; and determining the presence of any complex formed therebetween.

Also provided herein is an in vivo method of imaging cells expressing a polypeptide having the antibody binding specificity of the about 46 kDalton HMFG differentiation antigen and/or homology to at least one of the light chains of clotting factors V and VIII in a subject, the method comprising administering to a subject a polypeptide binding effective amount of an antibody having specificity of the about 46 kDalton HMFG differentiation antigen and/or homology to at least one of the light chains of clotting factors V and VIII or a functional fragment thereof under conditions effective to deliver it to an area of the subject's body suspected of having cells expressing the polypeptide or a functional fragment thereof to form an antibody-cell polypeptide complex;

administering to the subject a detectable label capable of binding to the antibody at a site other than the binding site for the polypeptide; and detecting the presence of label in the subject's body associated with any complex formed.

Also part of this invention is an in vivo method of vaccinating a subject with a polypeptide having the binding specificity of the about 46 kDalton HMFG differentiation antigen and/or homology to at least one of the light chains of clotting factors V and VIII or a functional fragment thereof, the method comprising administering to a subject a polypeptide having the antibody binding specificity of the about 46 kDalton HMFG differentiation antigen and/or homology to at least one of the light chains of clotting factors V and VIII or a functional fragment thereof in an amount and under conditions effective to vaccinate the subject against the polypeptide, functional fragments thereof or cells carrying the polypeptide or functional fragments thereof.

Yet another method is provided herein for detecting the presence of an antibody having specificity for the about 46 kDalton HMFG differentiation antigen in a biological sample, which comprises providing a sample suspected of comprising the antibody;

adding thereto an antibody binding effective amount of a polypeptide having the antibody binding specificity of the about 46 kDalton HMFG differentiation antigen and/or homology to at least one of the light chains of clotting factors V and VIII or a functional fragment thereof under conditions effective to form an antibody-polypeptide complex; and determining the presence of any complex formed therebetween.

This invention also relates to a second method of detecting the presence of an antibody having specificity for the about 46 kDalton HMFG differentiation antigen in a biological sample, comprising providing a sample suspected of comprising the antibody;

adding thereto an antibody binding effective amount of the fusion protein of this invention under conditions effective to form an antibody-fusion protein complex;

adding thereto a second polypeptide binding effective amount of an anti-second polypeptide antibody under conditions effective to form an antibody-fusion protein-antibody complex; and determining the presence of any antibody-fusion protein-antibody complex formed therebetween.

Also provided herein is an in vivo method of delivering a therapeutic agent to target cells expressing a polypeptide having the antibody binding specificity of the about 46 kDalton HMFG differentiation antigen and/or homology to at least one of the light chains of clotting factors V and VIII or a functional fragment thereof in a patient, the method, comprising binding a therapeutic agent to an antibody having specificity for a polypeptide having the antibody binding specificity of the about 46 kDalton HMFG differentiation antigen and/or homology to at least one of the light chains of clotting factors V and VIII or a functional fragment thereof at a site other than the polypeptide binding site; and administering to a subject suspected of carrying target cells a therapeutically effective amount of the antibody-bound therapeutic agent under conditions effective for reaching the cells' environment; and allowing for the antibody carrying the therapeutic agent to bind to the cells' polypeptide.

Still part of this invention is an ex vivo method of delivering a therapeutic agent to target cells expressing a polypeptide having the antibody binding specificity of the about 46 kDalton HMFG differentiation antigen and/or homology to at least one of the light chains of clotting factors V and VIII or a functional fragment thereof, comprising obtaining a biological sample suspected of comprising target cells from a subject;

binding a therapeutic agent to an antibody having specificity for a polypeptide having the antibody binding specificity of the about 46 kDalton HMFG differentiation antigen and/or homology to at least one of the light chains of clotting factors V and VIII or functional fragment thereof at a site other than the polypeptide binding site;

adding the antibody-bound therapeutic agent to the sample under conditions effective to promote the formation of an antibody-cell polypeptide complex; and returning the sample to the subject.

This invention also relates to a polynucleotide encoding a polypeptide having the antibody binding specificity of the about 46 kDalton HMFG differentiation antigen and/or homology to at least one of the light chains of clotting factors V and VIII or fragments thereof.

Also provided herein is a polyribonucleotide encoding a polypeptide having the antibody binding specificity of the about 46 kDalton HMFG differentiation antigen and/or homology to at least one of the light chains of clotting factors V and VIII or fragments thereof.

Still part of this invention are a polynucleotide and a polyribonucleotide encoding the fusion protein of tile invention or antibody binding functional fragments thereof.

This invention also relates to a DNA sequence which is complementary to a polynucleotide encoding a polypeptide having the antibody binding specificity of the about 46 kDalton HMFG differentiation antigen and/or homology to at least one of the light chains of clotting factors V and VIII or functional fragments thereof.

This invention also relates to a method of detecting the presence of a polynucleotide sequence encoding a polypeptide having the antibody binding activity of the about 46 kDalton HMFG differentiation antigen and/or homology to at least one of the light chains of clotting factors V and VIII or fragments thereof in a sample, the method comprising providing a sample suspected of comprising the polynucleotide;

melting double stranded polynucleotide present in the sample;

adding thereto a hybridization effective amount of a DNA sequence which is complementary to the polynucleotide encoding a polypeptide having the antibody binding activity of the about 46 kDalton HMFG differentiation antigen and/or homology to at least one of the light chains of clotting factors V and VIII or a fragment thereof in labeled form under conditions effective to hybridize any polynucleotide present in the sample having a complementary sequence thereto of at least 15 bases; and detecting the presence of the DNA-complementary polynucleotide hybrid.

Also provided by this invention is a method of detecting the presence of an RNA sequence encoding a polypeptide having the antibody binding specificity of the about 46 kDalton HMFG differentiation antigen and/or homology to at least one of the light chains of clotting factors V and VIII or a fragment thereof in a sample, comprising providing a sample suspected of comprising the RNA;

adding thereto a hybridization effective amount of a polynucleotide encoding a polypeptide having the antibody binding specificity of the about 46 kDalton HMFG differentiation antigen and/or homology to at least one of the light chains of clotting factors V and VIII or fragment thereof in labeled form under conditions effective to hybridize any RNA present in the sample having a complementary sequence of at least 15 bases thereto; and detecting the presence of the polynucleotide-RNA hybrid.

Also encompassed by this invention is a method of detecting the presence of an RNA sequence encoding a polypeptide having the antibody binding specificity of the about 46 kDalton HMFG differentiation antigen and/or homology to at least one of the light chains of clotting factors V and VIII or a fragment thereof in a sample, comprising providing a sample suspected of comprising the RNA;

adding thereto a hybridization effective amount of a polyribonucleotide sequence complementary to that of a polyribonucleotide encoding a polypeptide having the antibody binding specificity of the about 46 kDalton HMFG differentiation antigen and/or homology to at least one of the light chains of clotting factors V and VIII or fragment thereof in labeled form under conditions effective to hybridize any RNA having a complementary sequence thereto of at least about 15 bases; and detecting the presence of the complementary polyribonucleotide-RNA hybrid.

Also provided herein is a method of detecting the presence of a DNA sequence encoding a polypeptide having the antibody binding specificity of the about 46 kDalton HMFG differentiation antigen and/or homology to at least one of the light chains of clotting factors V and VIII or a fragment thereof in a sample, comprising providing a sample suspected of comprising the DNA;

melting double stranded polynucleotides in the sample;

adding thereto a hybridization effective amount of an RNA sequence encoding a polypeptide having the antibody binding specificity of the about 46 kDalton HMFG differentiation antigen and/or homology to at least one of the light chains of clotting factors V and VIII or a fragment thereof in labeled form under conditions effective to hybridize any DNA present in the sample having a complementary sequence thereto of at least 15 bases; and detecting the presence of the DNA-RNA hybrid in the sample.

Still part of this invention is a DNA segment comprising an anti-sense sequence to a polynucleotide encoding a polypeptide having the antibody binding specificity of the about 46 kDalton HMFG differentiation antigen and/or homology to at least one of the light chains of clotting factors V and VIII or a functional fragment thereof of about 15 to 2000 bases.

Moreover, also provided is a method of treating breast cancer in a subject in need of such treatment, the method comprising administering to the subject a composition comprising a therapeutically effective amount of the anti-sense DNA described above.

This invention also relates to an immunoassay kit comprising, in separate containers a monoclonal antibody having specificity for a polypeptide provided with the antibody binding specificity of the about 46 kDalton HMFG differentiation antigen and/or homology to at least one of the light chains of clotting factors V and VIII or a functional fragment thereof; and anti-antibody immunoglobulin.

Still part of this invention is an antibody detecting kit comprising, in separate containers a polypeptide provided with the antibody binding specificity of the about 46 kDalton HMFG differentiation antigen and/or homology to at least one of the light chains of clotting factors V and VIII or a functional fragment thereof; and anti-antibody immunoglobulin.

A fusion protein kit is also provided herein which comprises, in separate containers a fusion protein comprising a polypeptide having the binding specificity of the about 46 kDalton HMFG differentiation antigen and/or homology to at least one of the light chains of clotting factors V and VIII or fragments thereof and a second antigenic polypeptide or fragments thereof which is bound thereto;

an anti-second polypeptide polyclonal or monoclonal antibody; and anti-antibody immunoglobulin.

Also encompassed by this invention is an anti-breast cancer therapeutic kit comprising, in separate containers a monoclonal antibody having specificity for a polypeptide provided with the antibody binding specificity of the about 46 kDaltons HMFG differentiation antigen and/or homology to at least one of the light chains of clotting factors V and VIII; and an anti-cancer therapeutic agent selected from the group consisting of immunotoxins and radionuclides.

A more complete appreciation of the invention and many of the intended advantages thereof will be readily perceived as the same becomes better understood by reference to the following detailed description when considered in connection with the accompanying figures.

BRIEF DESCRIPTION OF THE DRAWINGS

The FIGURE shows the expression of BA46-1 specific mRNA in human carcinoma cell lines. Total RNA (20ug/ lane) was run on a 1.4% agarose gel, blotted, and hybridized to 32P labelled RNA generated from the BA46-1 cDNA clone. The contents of the samples in the different lanes are as follows: a) A549 (lung); b) BT20 (breast); c) ELLG (breast); d) Raji (lymphoid); e) SKBR3 (breast); f) SKOV3 (ovary); g) MDA-MB-361 (breast); h) MDA-MB-331 (breast) i) HeLa (cervix); j) HS578T (breast); k) HT29 (colon); l) PanCl (pancreas); m) MCF7 (breast). Exposure was 16 hours with an intensifying screen.

Other objects, advantages and features of the present invention will become apparent to those skilled in the art from the following discussion.

BEST MODE FOR CARRYING OUT THE INVENTION

Figure 1:
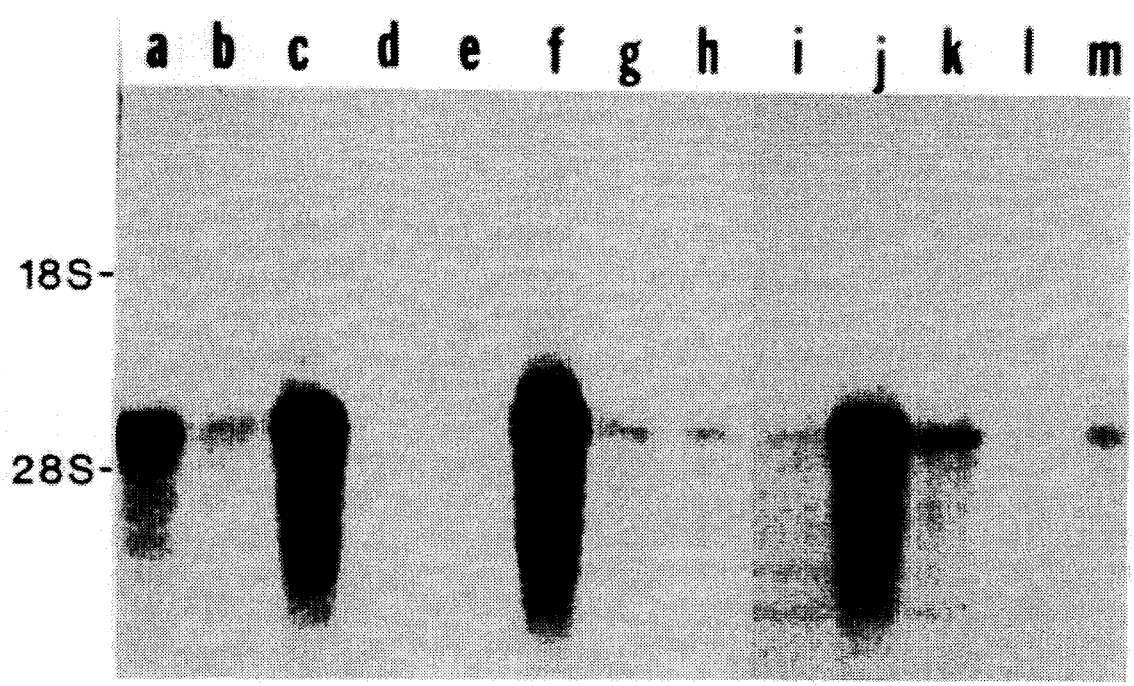

This invention arose from a desire to improve on technology useful for detection, diagnosis, and treatment of breast cancer.

This work relies on the isolation of a cDNA clone (BA 46-1) that encodes a portion of all about 46 kDalton polypeptide component of the HMFG system and monoclonal antibodies that bind the about 46 kDalton component of the HMFG system. These monoclonal antibodies have specificity for, and bind to the BA 46-1 cDNA encoded portion of a fusion protein also containing β-galactosidase and made from the BA 46-1 lambda/gt11 clone.

The nucleotide and deduced amino acid sequence of the BA 46-1 cDNA is shown in Table 1 in Example 6 below. The partial sequence is about 217 amino acids long having a theoretical molecular weight of about 25 kDaltons and, represents the C-terminus of the complete protein. In this sequence, there are 4 potential sites for N-linked glycosylation. The sequence is asparagine and leucine rich. Starting from the C-terminus, the nucleotide sequence extends to the 3' end of the mRNA which contains the AATATA consensus sequence preceeding the poly (A) sequent for cleavage and polyadenylation.

A comparison of the nucleotide sequence to sequences in the EMBL database using FSTNSCAN (PCGENE) revealed extended homology with human serum factors V and VIII, and with protein C. The deduced protein sequence, however, shares identity only with factors V and VIII but not with protein C since the homology at the nucleotide level is found in an intervening sequence (See, Table 2). There is an about 43% identity of the BA 46 to factor V and an about 38% identity to factor VIII. The regions of factors V and VIII shown in Table 2 share an about 47% identity.

The results of the analysis of the deduced amino acid sequence of the about 46 kDalton protein are consistent with that of a glycosylated protein. The function of this protein, however, remains unknown. The homology with the clotting factors may be found in the C1, C2 region of the light chain of factor VIII. Human antibodies that bind this region of the light chain of factor VIII inhibit the factor by preventing its interaction with phospholipids. Since this region of factor VIII has been implicated in phospholipid binding, it is likely that the homologous region in the about 46 kDalton protein may serve a similar role.

The appearance of a shared domain in otherwise different proteins may be due to exon shuffling. The C-terminus may serve as a novel "anchor" sequence for the about 46 kDalton protein or it may be involved in binding of mucin and/or cell membrane to the phospholipids found on the surface of growing milk fat droplets. Alternatively, the homologous sequence may be involved in the assembly of the mucin complex at the plasma membrane surface.

The single stranded RNA probe provided herein is complementary to the ORF found in the cDNA insert. That is, in frame with the β-galactosidase DNA sequence in the lambda/gt11 vector. This indicates that this ORF represents the sense strand of the BA 46-1 gene since only the complementary strand probe binds to a specific 2.2 kilobase mRNA of epithelial cell lines.

The BA 46-1 β-galactosidase fusion protein expressed by the lambda/gt11 clone is useful for assaying the presence of the about 46 kDalton HMFG polypeptide component or fragments thereof in serum obtained from breast cancer patients. This fusion protein is also useful as an immunogen for generating second generation monoclonal and polyclonal antibodies. These antibodies may be used, among other applications, to further study the tissue distribution of this antigen and how it relates to the synthesis of its messenger RNAs, to provide improved immunoassays, and to purify and characterize the about 46 kDaltons antigen polypeptide.

Some monoclonal antibodies raised against the about 46 kDalton protein can detect the respective epitopes present on this molecule by radioimmunobinding assays on HMFG membranes and on breast carcinoma membrane material These monoclonal antibodies do not stain normal breast tissue by immunohistology nor any other normal tissues tested. However, some of them weakly stain 24 of 49 breast carcinomas and are negative on all other carcinomas tested. Since some breast carcinomas have very high levels of mRNA for the about 46 kDalton antigenic component, it is possible that antibodies made against the fusion protein have different, and possibly improved, specificity for detecting the about 46 kDalton antigenic component by immunohistophathology.

Northern blots using the cDNA clone in the present work clearly show that the mRNA for this antigen is present in 8 out of 9 breast carcinoma cell lines tested, and in several other non-breast carcinoma cell lines. The RNA for the antigen is, however, present at much lower levels in a lymphoid cell line (Raji). There is considerable variation in the observed expression levels of the about 2.2 kbase RNA detected in the carcinoma cell lines. The lung cells (A549), ovary cells (SKOV3) and two breast cell lines (E11-G and HS578T) accumulate much more of this transcript than other carcinoma cell lines. Overexpression of certain genes, such as Her 2/neu, and the EGF receptor in breast and other carcinomas has been correlated with prognosis. Overexpression of the about 46 kDalton protein in carcinomas may very well correlate with outcome of disease. The about 46 kDalton antigenic component thus shows epithelial specificity. This, however, does not imply that certain epitopes of the molecule may not have greater breast specificity. Moreover, since it is known that there is often a deregulation of expression of many cell antigens associated with malignancy, the expression of this antigen mRNA in non-breast carcinomas does not imply that the antigen is actually expressed nor that the antigen is found in the normal epithelial cells which are counterparts to cells in these epithelial tumors.

Having cloned a portion of the cDNA of this molecule permitted the further deduction of the sequence of the encoded polypeptide. It also permitted the synthesis of recombinant proteins or synthetic peptides from the known amino acid sequence as well as the preparation of a new generation of monoclonal antibodies against specific epitopes of this polypeptide. Also possible with the preparation of the fusion DNA and fusion protein of the invention is the further preparation of polyclonal and monoclonal antibodies against the fusion protein that can be selected to be of greater breast specificity. The HMFG membrane system, in fact, truly represents a purified portion of the apical surface of the normal breast epithelial cell. The about 46 kDalton component being a major molecular species of the HMFG membrane thus also represents a major and perhaps important component of the apical surface of the normal breast epithelial cell.

The cDNA clones of the about 46 kDalton polypeptide component of the HMFG system allowed the deduction of the amino acid sequence of its corresponding polypeptide. These cDNA clones also allowed the preparation of a new generation of monoclonal antibodies that have sufficient specificity for application to breast cancer immunotherapy, sufficient staining ability in immunohistopathology, for histological evaluation of specificity and prognostic and diagnostic ability, and ability to identify the about 46 kDalton HMFG peptide component or functional fragments thereof in the serum of breast cancer patients, for the construction of serum assays for diagnosis of breast cancer, and the screening for early detection of the disease.

This invention thus provides a polypeptide having the antibody binding specificity of the about 46 kDalton HMFG differentiation antigen and/or homology to at least one of the light chains of clotting factors V and VIII. In one preferred embodiment the polypeptide has tile biological activity of the about 46 kDalton HMFG antigen molecule, and more preferably the polypeptide comprises the 46 kDalton HMFG differentiation antigen or an antibody binding functional fragment thereof The polypeptide of the invention may be about 90 to 500 amino acids long, preferably about 200 to 450 amino acids long, and more preferably about 220 to 420 amino acids long.

In another preferred embodiment the polypeptide has the amino acid sequence shown in Table 2 or an antibody binding functional fragment thereof, preferably of about 5 to 100 amino acids long, and more preferably 15 to 50 amino acids long. Particularly preferred are amino acid sequences which correspond to the specific epitopes which are recognized by anti 46 kDalton HMFG differentiation antigen antibodies.

Also provided herein is a pharmaceutical composition, which comprises an antibody binding effective amount of the polypeptide described above; and a pharmaceutically acceptable carrier.

This pharmaceutical composition is intended for animal, including human, administration. Each dose preferably contains about 0.1 to 1000 mg of the polypeptide, and more preferably about 10 to 500 mg. Any pharmaceutically acceptable carrier can be utilized for the preparation of the composition. Examples of suitable carriers and other additives are flavorings, preservatives, colorants, salt solutions such as saline, oils or solids, among others. However, any liquid or solid carrier which does not hydrolyze the polypeptide is suitable. The pharmaceutical composition as well as the polypeptide itself are best kept under refrigeration and/or frozen. The polypeptide and the pharmaceutical composition may be vacuumed dried and packaged in a sterile container for transportation to their destination. The composition may comprise about 0.01–99.99 wt % of the polypeptide, and preferably about 0.1–10 wt %, the remainder being the carrier.

Also provided herein is a fusion protein, which comprises
    the polypeptide described above; and
    a second antigenic polypeptide or an antibody binding functional fragment thereof which is operatively linked or bound to the polypeptide of the invention.

The fusion protein may generally be composed of an antibody binding functional fragment of the polypeptide of the invention bound to an antibody binding functional fragment of the second antigenic polypeptide, which are about 6 to 700 amino acids long and 1500 amino acids long, respectively, and preferably about 15 to 100 amino acids long and 200 to 400 amino acids long, respectively. However, other sizes of the polypeptides, and/or fragments thereof, either larger or smaller, may be utilized as long as their antibody binding capability is preserved.

Any polypeptide is suitable as the second antigenic polypeptide as long as it acts as an antigen to elicit the formation of antibodies by a mammal as is known in the art. The second antigenic polypeptide may be chosen in addition because it possesses some other property which is of use for the identification and/or use of the fusion protein. By means of example the second antigenic polypeptide may be a protein such as β-galactosidase or a functional fragment thereof. However, any other second antigenic polypeptide may be utilized as long as antibodies to it can be raised. For example, gene 10 from bacteriphage T7 may also be used.

Both, the polypeptide of the invention and the fusion protein may be prepared by methods known in the art. By means of example, the polypeptide may be prepared synthetically or it may be produced by the expression of a DNA fragment that encodes it which can be cloned into a vector and inserted into a host capable of expression. (Marston, F. A., in DNA cloning: A practical approach, Glover, P., ed., IRL Press, London, Vol. 3, pp. 59–88 (1987)). The fusion protein may be prepared by providing a recombinant DNA containing sequences which encode the amino acid sequences of the two polypeptides. This DNA may be cloned into a vector and expressed in a host.

Also part of this invention is an antibody having specificity for a polypeptide having the antibody binding specificity of the about 46 kDalton HMFG differentiation antigen and/or homology to at least one of the light chains of clotting factors V and VIII.

Methods for raising antibodies are known in the art and need not be described herein. Particularly preferred are antibodies which are monoclonal antibodies. Methods of preparing monoclonal antibodies against a specific polypeptide are also known in the art and need not be described in detail herein.

The antibodies raised against the biologically pure polypeptide or fragments thereof have increased affinity and/or specificity for the polypeptide. Typically, the affinity may be about 10–8 to 10–5, and in some cases greater than 10–8.

In a particularly preferred embodiment of the invention tile antibody also has affinity for the C1 and/or C2 regions of clotting factor VIII (light Chain). Still another preferred embodiment is that wherein the antibody of the invention is the Fab fragment thereof, with its binding capacity preserved. Also, preferred are a single chain of the antibody, or the Fab fragment having the described functionality and functional fragments thereof.

Also provided herein is a pharmaceutical composition, which comprises a polypeptide binding effective amount of an antibody having an affinity of about 10–10 to 10–5 for a polypeptide provided with tile antibody binding specificity of the about 46 kDalton differentiation antigen and/or homology to at least one of the light chains of clotting factors V and VIII of the HMFG system; and
   a pharmaceutically acceptable carrier.

Typically, the antibody is provided in an amount of about 0.001 to 10,000 mg, and more preferably about 10 to 500 mg. Any pharmaceutically acceptable carrier is suitable as indicated above. Other ingredients may also be contained in the composition such as radionuclides, chemotherapeutic drugs, interferon, toxic agents such as ricin A-chain, abrin A-chain, saline salt solutions, preservatives, flavors, colorants and buffers, among others, as is known in the art. The preparation of the pharmaceutical composition can be undertaken as is known in the art by admixing the polypeptide or the antibody with the pharmaceutically-acceptable carrier in the absence of hydrolyzing conditions, then vacuum dried and packaged in a sterile container or provided as a sterile solution.

Also part of this invention is a method of detecting tile presence in a biological sample of a polypeptide having the antibody binding activity of the about 46 kDalton HMFG differentiation antigen and/or homology to at least one of the light chains of clotting factors V and VIII or a functional fragment thereof, comprising providing a biological sample suspected of comprising the polypeptide;
   adding thereto a polypeptide binding effective amount of an antibody having specificity for a polypeptide having the antibody binding specificity of the about 46 kDalton HMFG differentiation antigen and/or homology to at least one of the light chains of clotting factors V and VIII; under conditions effective to form an antibody-polypeptide complex; and
   determining the presence of any complex formed.

This method is suitable for detecting the presence of the polypeptide in biological samples such as animal cells, cell extracts or body fluids. Typically, any body fluids are encompassed herein. Examples are serum, plasma, urine, breast fluid, tissue biopsies, and fine needle aspirates.

The sample may be previously treated, e.g., to avoid interference by metals, non-specific proteins, fats, nucleic acids, and the like.

The biological sample may also be diluted in order that the content of the polypeptide be in a range of about 0.0001 to 10 mg/ml, and more preferably about 0.001 to 0.1 mg/ml. The antibody may be added as known in the art in an amount of about 0.0001 to 1.0 mg/ml of sample, and more preferably about 0.001 to 0.1 mg/ml of sample.

Other conditions for the assay may be as follows. The sample may be homogenized and centrifuged to remove particulate material and fatty material. Detergents may be added to dissolve membranes, solubilize fatty material and reduce background. Also added may be carrier proteins such as bovine serum albumin to reduce non-specific binding of the antibodies, and chelators to remove interfering divalent metal ions.

The determination of the presence of any complex formed between the antibody and the polypeptide may be done by a variety of methods known in the art. By means of example will be cited herein the further addition of a labeled anti-antibody immunoglobulin to form a double antibody-polypeptide complex which is labeled. The label may be a radiolabel, a fluorescent label, an enzyme label or biotin to be later detected as a conjugate of avidin, streptavidin or magnetic bead. After this step the amount of label bound to the complex may be assessed by methods known in the art.

Also provided herein is a method of determining the presence in a biological sample of epithelial cells, which comprises providing a biological sample suspected of comprising cells of epithelial origin carrying a polypeptide having the antibody binding activity of the about 46 kDalton HMFG differentiation antigen and/or homology to at least one of the light chains of clotting factors V and VIII or a functional fragment thereof;
   adding thereto a polypeptide binding effective amount of an antibody laving specificity for a polypeptide having the antibody binding specificity of the about 46 kDalton differentiation antigen and/or homology to at least one of the light chains of clotting factors V and VIII of the HMFG system under conditions effective to form an antibody-cell polypeptide complex; and
   determining the presence of any complex formed.

This method is particularly well suited for biological samples such as bone marrow samples. However, it may be practiced with samples of other origin as well. The steps are in general conducted as described above and the determination of the presence of epithelial cells may be done by the identification, either qualitative or quantitative, of any complex formed with the antibody as already described.

The detection may also be undertaken by assaying for the presence of ribonucleic acid (RNA) encoding the about 46 kDalton protein using nucleic acid probes based on sequences such as the one shown in Table 1 and methods known in the art such as PCR (Erlich, H.A., in PCR Technology: Principles and Applications for DNA Amdification, 1989, Stockton Press).

Also provided herein is an in vivo method of imaging cells expressing a polypeptide having the antibody binding specificity of the about 46 kDalton differentiation antigen of the HMFG system and/or homology to at least one of the light chains of clotting factors V and VIII in a subject, the method which comprises administering to a subject a polypeptide binding effective amount of an antibody having specificity for a polypeptide with the antibody binding specificity of the about 46 kDalton HMFG differentiation antigen and/or homology to at least one of the light chains of clotting factors V and VIII under conditions effective to deliver it to an area of the subject's body suspected of having cells expressing the polypeptide to form an antibody-cell polypeptide complex;
   administering to the subject a detectable label capable of binding to the antibody at a site other than binding site of the polypeptide; and detecting the presence of the label associated with any complex formed in the subject's body.

The administration of the antibody may be at a concentration of about 0.5 to 50 mg/ml, and more preferably about 5 to 20 mg/ml. A total of about 10 to 50 ml of the antibody composition may be given at any one particular time. The regimen of administration may be a single dose or the antibody may be administered in a continuous manner in order to continuously suppress the presence of polypeptide or functional fragments thereof in the subject's cells. Thus, repeated doses of the antibody composition are also contemplated.

The antibody may be administered in a pharmaceutical composition as described above, or in any other form found suitable. The administration of the antibody may be conducted by the intravenous, intraperitoneal, intracavitary, lymphatic, intratumor and intramuscular routes, among others. Other routes as suitable may also be utilized which will not hydrolyze the peptide links of the antibody.

The administration of a detectable label may be conducted by providing an anti-antibody immunoglobulin or a binding-functional fragment thereof which is labeled and then detecting the amount of label bound to the complex. These technologies are known in the art and need not be further described herein.

Also provided herein is a method of detecting a presence in a biological sample of an antibody having affinity for the about 46 kDalton HMFG differentiation antigen, comprising providing a sample suspected of comprising the antibody;

adding thereto an antibody binding effective amount of a polypeptide having the antibody binding specificity of the about 46 kDalton HMFG differentiation antigen and/or homology to at least one of the light chains of clotting factors V and VIII under conditions effective to form an antibody-polypeptide complex; and determining the presence of any complex formed.

The method described above utilizes tile polypeptide of the invention in order to detect the presence of antibodies in a mammal generated as a consequence of the presence of such polypeptide in the mammal's body. The sample may be treated as indicated above to eliminate interference of other proteins and/or components of the sample. In the case of blood, serum may be obtained first, and then the serum may be treated as follows.

Normal human or bovine serum may be added, and/or bovine serum albumin (BSA) is used as a blocking agent to reduce non-specific reactivity.

The polypeptide is added to the sample in an amount of about 0.00001 to 1.0 mg/ml of sample, and more preferably about 0.0001 to 0.1 mg/ml of sample. However, other amounts may also be utilized as seen suitable. The amount of antibody in the sample may be controlled by dilution. Optimal ranges of antibody in the sample are about 0.00001 to 0.1 mg/ml, and more preferably about 0.0001 to 0.01 mg/ml. However, other amounts may also be utilized. The steps of this method are practiced as described above, including the determination of the presence of antibody-polypeptide complex. The conditions for the assay are in general those known in the art, such as pH temperature and the like.

Also provided herein is a method of detecting the presence of an antibody having affinity for the about 46 kDalton HMFG differentiation antigen in a sample, the method comprising providing a sample suspected of comprising the antibody;

adding thereto an antibody binding effective amount of a fusion protein comprising a polypeptide having the antibody binding specificity of the about 46 kDalton HMFG differentiation antigen and/or homology to at least one of the light chains of clotting factors V and VIII and a second antigenic polypeptide or an antibody binding functional fragment thereof bound to one another under conditions effective to form an antibody-fusion protein complex;

adding thereto a second polypeptide binding effective amount of an anti-second polypeptide antibody under conditions effective to form an antibody-fusion protein-antibody complex; and determining the presence of any antibody-fusion protein-antibody complex form.

As in the case of the previous methods this method is practiced preferably with a monoclonal antibody. The amounts of antibody added to the sample are preferably about 0.00001 to 0.1 mg/ml sample, and more preferably about 0.0001 to 0.01 mg/ml of sample. However, other amounts may also be utilized. As in the previous cases the sample may be pretreated prior to the addition of the fusion protein. One example is the dilution of the sample and the elimination of interfering components. These steps are undertaken as is known in the art and need not be further described herein.

Also provided herein is an in vivo method of vaccinating a subject with a polypeptide having the binding specificity of the about 46 kDalton HMFG differentiation antigen and/or homology to at least one of the light chains of clotting factors V and VIII or a functional fragment thereof, comprising administering to a subject to be vaccinated a polypeptide having the antibody binding specificity and/or homology to at least one of the light chains of clotting factors V and VIII of the above 46 kdalton HMFG differentiation antigen or a functional fragment thereof in an amount and under conditions effective to vaccinate the subject against the polypeptide, functional fragments thereof or cells carrying the polypeptide or functional fragments thereof. This in vivo method may be utilized to vaccinate a cancer patient against a polypeptide of the described characteristics or cells carrying it. In this manner the patient is induced to raise an immune response against the polypeptide or cells carrying the polypeptide.

The vaccinating polypeptide may be administered to the subject in an amount of about 0.1 to 100 mg/ml, and more preferably about 2 to 50 mg/ml. Typically, any dose will consist of about 0.1 to 50 ml of the vaccinating polypeptide, and more preferably about 2 to 10 ml. The vaccinating agent may be administered in a single dose or it may be administered on a continuous basis for periods of up to about 6 months, and sometimes in excess of one year. More prolonged periods of time are also encompassed for vaccination according to this invention.

Also provided herein is an in vivo method of delivering a therapeutic agent to target cells expressing a polypeptide having the antibody binding activity and/or homology to at least one of the light chains of clotting factors V and VIII of the about 46 kDalton HMFG differentiation antigen in a patient, comprising binding to a monoclonal antibody having specificity for a polypeptide provided with tile antibody-binding specificity of the about 46 kDalton HMFG differentiation antigen and/or homology to at least one of the light chains of clotting factors V and VIII a therapeutic agent at a site other than the polypeptide binding site;

administering to a subject suspected of carrying the target cells a therapeutically effective amount of the antibody-bound therapeutic agent under conditions effective to deliver the agent to the cells' environment; and allowing for the antibody carrying the therapeutic agent to bind to the cells' polypeptide to permit therapeutic agent to exert its effect on the cells.

This in vivo method may be utilized for treating cancer patients that are afflicted with cancer to epithelial cells, e.g., breast cancer.

The therapeutic agent may be any anti-cancer agent known in the art. Examples of therapeutic agents are radionuclides, chemotherapy drugs, toxic agents such as ricin A-chain, abrin A-chain, etc. However, others may also be utilized. The therapeutic agent is bound to the antibody by means known in the art. More specifically, a radionuclide such as 131I is bound to the antibody by oxidation of amino acids such as tyrosine, or 90 Y attached via a chelator, and the conjugate injected intravenously or intraperitoneally into humans carrying human breast tumors, and the growth of the tumor is thus inhibited. (e.g., for mice, Ceriani, et al, Cancer Res. 48:4664–4672(1988)).

The antibody-bound therapeutic agent may be administered to the subject in an amount of about 1 to 100 mg of composition/ml, and more preferably about 2 to 20 mg of composition/mi. Typically, any dose will consist of about 1 to 50 ml of antibody-bound therapeutic agent containing composition and more preferably about 2 to 10 ml. The therapeutic agent may be administered as an antibody-bound agent in a single dose or it may be administered on a continuous bases for periods of up to about 6 months, and sometimes in excess of one year. More prolonged periods of time are also encompassed for treatment herein.

Also provided herein is an ex vivo method of delivering a therapeutic agent to target cells expressing a polypeptide having the antibody binding activity of the about 46 kDalton HMFG differentiation antigen and/or homology to at least one of the light chains of clotting factors V and VIII, the method which comprises obtaining from a subject a biological sample suspected of comprising target cells;

binding to a monoclonal antibody having specificity for a polypeptide provided with the antibody binding specificity of the about 46 kDalton HMFG differentiation antigen and/or homology to at least one of the light chains of clotting factors V and VIII a therapeutic agent at a site other than the polypeptide binding site;

adding the antibody-bound therapeutic agent to the sample under conditions effective to promote the formation of an antibody-cell polypeptide complex;

allowing the agent to exert its effect on the cells;

and returning the sample to the subject.

The non-conjugated antibody may also be added to the sample in the presence of complement, which causes lysis of the cells, prior to returning the sample to the subject.

In general the steps of this method may be practiced as described above, particularly in terms of the preparation of the biological sample, and binding of the therapeutic agent to the antibody as well as the addition of the antibody-bound therapeutic agent to the sample. With respect to the return of the sample to the subject, this may be done by means known in the art. For example, the already treated sample may be returned to a subject's body in sterile form by the intravenously, intracavitary, intraperitoneal, and intratumor routes. However, other routes known in the art may also be utilized.

Also provided herein is a polynucleotide encoding a polypeptide having the antibody binding specificity of the about 46 kDalton HMFG differentiation antigen of the invention and/or homology to at least one of the light chains of clotting factors V and VIII or binding functional fragments thereof. The polynucleotide is provided either as a double stranded DNA or as a single stranded DNA containing the coding strand of the polynucleotide. The fragments of the polynucleotide may be of about 15 to 2000 bases, and more preferably about 30 to 300 bases.

Also provided herein is a DNA sequence which is complementary to the coding strand of the polynucleotide described above.

Both the double stranded and the single stranded DNAs discussed above are also provided in labeled form. The labeling may be conducted as is known in the art with radioactive atoms such as 32P,14C, 3H, and the like. However, other radionuclides may also be utilized.

Particularly preferred is a polynucleotide having the DNA sequence shown in Table 1 of this patent or fragments thereof or DNA sequences comprising about 9 to 2000 bases, and more preferably about 18 to 200 bases. However, fragments of other sizes may also be utilized and are encompassed herein.

Also part of this invention is a polyribonucleotide encoding a polypeptide having the antibody binding specificity and/or homology to at least one of the light chains of clotting factors V and VIII of the about 46 kDalton HMFG differentiation antigen or fragments thereof. This is the coding RNA for the polypeptide.

The polyribonucleotide sequences may be of a size of about 9 to 3000 bases long, and more preferably fragments of about 18 to 300 bases long. However, other fragment sizes are also encompassed herein.

Still part of this invention is a non-coding strand of a polyribonucleotide having a sequence complementary to that of the polyribonucleotide described above. This polyribonucleotide sequence is capable of hybridization to the coding RNA strand or to the non-coding strand of the corresponding DNA. In a particularly preferred embodiment the polyribonucleotide is provided in labeled form.

Also part of this invention is a polynucleotide encoding a fusion protein comprising a polypeptide having the antibody binding specificity of the about 46 kDalton HMFG differentiation antigen and/or homology to at least one of the light chains of clotting factors V and VIII and a second antigenic polypeptide or an antibody binding functional fragment thereof bound to one another.

The polynucleotide may be about 400 to 4000 bases long, and more preferably about 500 to 1,400 bases long. However, other size polynucleotides are also encompassed herein.

Also provided herein is a polyribonucleotide encoding a fusion protein comprising a polypeptide provided with the antibody binding specificity of the about 46 kDalton HMFG differentiation antigen and/or homology to at least one of the light chains of clotting factors V and VIII and a second antigenic polypeptide, or an antibody binding functional fragment thereof bound to one another. Also, a polyribonucleotide is provided which is complementary to the sequence of the RNA encoding the fusion protein.

The polyribonucleotide encoding the fusion protein may be about 400 to 4000 bases long, and more preferably about 500 to 1,400 bases long. Fragments thereof may be about 9 to 100 long, and more preferably about 15 to 70 bases long.

Still part of this invention is a polynuclectide encoding the fusion protein of the invention or functional fragments thereof about 15 to 4000 bases long, and more preferably about 50 to 1800 bases long. The polynucleotide encoding the fusion protein is provided as a double stranded DNA or as a single stranded DNA which encompasses the coding strand of the fusion protein and a second polynucleotide encompassing a sequence corresponding to the non-coding DNA strand or fragments thereof. The latter polynucleotide provided herein is a polynucleotide comprising DNA sequences complementary to the polynucleotide encoding the fusion protein. Both the DNA and RNA sequences encoding the fusion protein may be provided in labeled form. Particularly useful labels are 32P and others known in the art. The DNAs and RNAs are labeled by methods known in the art.

Also provided herein is the method of detecting the presence in a sample of the polynucleotide sequence encoding a polypeptide having the antibody binding activity of the about 46 kDaltons HMFG differentiation antigen and/or homology to at least one of the light chains of clotting factors V and VIII, the method comprises providing a sample suspected of comprising the polynucleotide;

melting double stranded polynucleotide present in the sample;

adding thereto a hybridization effective amount of a DNA sequence which is complementary to the coding strand of a polynucleotide encoding the polypeptide of the invention in labeled form under conditions effective to hybridize any polynucleotide having a complementary sequence of at least 15 bases thereto; and detecting the presence of the DNA-complementary polynucleotide hybrid.

The sample subjected to this method may be a biological sample or it may be a sample generated in the laboratory. If the sample contains cells where the polynucleotide is located, the cells need to be lysed, and optionally the DNA isolated from the remainder materials. This is done by methods known in the art.

The sample may be further diluted and/or prepared for the melting of double stranded polynucleotide sequences present therein. The melting step is conducted as is known in the art. In general, the sample is prepared by lysing the cells in 4M guanidinium isothiocyanate to denature protein and prevent RNAse activity. Extracts are run on a Cesium Chloride density step gradient ultracentrifugation where RNA, DNA and protein are separated according to their relative densities. DNA and RNA are further purified by extraction with organic solvents, and concentrated by precipitation in 70% ethanol. (Sambrook et al, in Molecular Cloning: A Laboratory Manual, Second edition, Cold Spring Harbor Press, N.Y., (1989)). Melting is accomplished by raising the temperature of the sample about 20° C. over the Tm of the DNA, or by raising the pH to above 12.

To the melted DNA is added a hybridization effective amount of labeled DNA complementary to the coding strand of a polynucleotide encoding a polypeptide provided with the antibody binding specificity of the about 46 kDalton HMFG differentiation antigen and/or homology to at least one of the light chains of clotting factors V and VIII. The conditions for suitable hybridization of DNA-DNA segments are known in the art. The degree of stringency is determined by the number of complementary sequences desired to be hybridized. In general when more stringent conditions are utilized hybridization will occur with DNA sequences which have a higher degree of complementarily with the probe. Thus, when a low degree of stringency is desired to detect sequences with low complementarily, the conditions may be varied accordingly. In general, the conditions may be as follows.

The general conditions may be varied but are generally as follows. The sodium ion concentration is about 1M, the pH about 5–9, the temperature about 65° C. or about 20° C. below the melting temperature of the duplex DNA of the probe sequence and its complementary strand (Britten, R. et al, Methods in Enzymology 29:363(1974); Sambrook et al, supra).

The DNA-complementary polynucleotide labeled hybrid may be detected by methods known in the art. Typically, the double stranded DNA is restricted with enzymes and run on an electrophoresis gel to separate the different size strands. The gel is blotted onto a specially prepared filter, hybridized, and the filter is then exposed to a photographic plate for a period of time effective to obtain a picture thereof. The plate is then developed and the different fragments analyzed.

For a more qualitative detection of the presence of the double stranded labeled hybrid, the unrestricted DNA may be blotted onto a filter, hybridized, exposed to a photographic plate and the plate developed to merely detect the presence of radiolabel.

Also provided herein is a method of detecting the presence of an RNA sequence encoding a polypeptide having the antibody binding activity of the about 46 kDalton HMFG differentiation antigen and/or homology to at least one of the light chains of clotting factors V and VIII or a fragment thereof in a sample, comprising providing a sample suspected of comprising the RNA;

adding thereto a hybridization effective amount of the coding strand of a labeled polynucleotide encoding a polypeptide with the antibody binding specificity of the about 46 kDalton HMFG differentiation antigen and/or homology to at least one of the light chains of clotting factors V and VIII in single stranded form under conditions effective to hybridize any RNA having a complementary sequence of about at least 15 bases thereto; and detecting the presence of the polynucleotide-RNA hybrid.

In essence, the above method is conducted in a manner similar to the previously described method of detecting the presence of a DNA sequence, with the additional precaution of substantially ensuring a lack of degradation of the RNA contained in the sample. In general, the following must be additionally done when detecting RNA.

The use of RNAse inhibitors and the pretreatment of labware with diethylpyrocarbonate to inactivate any contaminating RNAses. Hybridizations are conducted generally at a higher stringency because RNA:RNA hybrids are more stable than DNA:DNA hybrids. For example, the hybridization may be conducted at 65° C. in 50% formamide. The Tm of DNA duplexes is reduced by about 0.72° C. per 1% formamide added. (See, Sambrook et al, supra; Casey J. and Davidson N., Nucl. Acids Res. 4:1539–1552(1977)).

If the RNA is contained inside the cells, the cells must be lysed to expose the ribonucleic acid. This is done by means known in the art such as detergent lysis, which may be followed by treatment with proteases.

Also part of this invention is a method of detecting the presence in a sample of an RNA sequence encoding a polypeptide having the antibody binding activity of the about 46 kDalton HMFG differentiation antigen and/or homology to at least one of the light chains of clotting factors V and VIII or a fragment thereof, the method comprising providing a sample suspected of comprising the RNA;

adding thereto a hybridization effective amount of a labeled oligoribonucleotide complementary to at least a portion of a polyribonucleotide sequence encoding a polypeptide provided with the antibody binding specificity of the about 46 kDalton HMFG differentiation antigen and/or homology to at least one of the light chains of clotting factors V and VIII under conditions effective to hybridize thereto RNA having a complementary sequence of at least about 15 bases; and detecting the presence of the polyribonucleotide-RNA hybrid.

This method is in general practiced in a manner similar to the two previous methods except that in this case precautions must be taken not to permit any degradation of the RNA sequences present in the sample and tile probe. The conditions for RNA-RNA hybridization are known in the art. In general, the conditions utilized involve a temperature of about 65° C. and about 50% formamide (mentioned above).

When the RNA is contained inside cells, the cells must be lysed to permit the exposure of the RNA.

A method of detecting the presence in a sample a polynucleotide sequence encoding a polypeptide having the antibody binding activity of the about 46 kDalton HMFG differentiation antigen and/or homology to at least one of the light chains of clotting factors V and VIII or fragments thereof is also part of this invention. The method comprises providing a sample suspected of comprising the polynucleotide;

melting double stranded polynucleotide present in the sample;

adding thereto a hybridization effective amount of a labeled RNA sequence encoding a polypeptide provided with the antibody binding specificity of the about 46 kDalton HMFG differentiation antigen and/or homology to at least one of the light chains of clotting factors V and VIII under conditions effective to hybridize thereto any polynucleotide having a complementary sequence thereto of at least about 15 bases; and detecting the presence of the RNA-complementary polynucleotide hybrid.

When the polynucleotide is inside the cells, the cells may be lysed to expose the DNA.

Also part of this invention is a DNA segment comprising an anti-sense sequence to the coding strand of a polynucleotide encoding a polypeptide having the antibody binding specificity of the about 46 kDalton HMFG differentiation antigen and/or homology to at-least one of the light chains of clotting factors V and VIII of about 200 to 3,000 nucleotides. More preferably, the DNA segment may have about 100 to 1,000 nucleotides.

The concept of anti-sense sequences is known in the art. Synthetic oligonucleotides may be prepared that are complementary to the messenger RNA encoding a target protein. The oligonucleotide or a chemically modified equivalent thereof are added to cells. The oligonucleotide binds the target mRNA and thus inhibits the translation of the target protein. (Markus-Sekura C. J., Techniques for using Antisense Oligonucleotides to Study Gene Expression, Analytical Biochemistry 172:289–295(1988)).

Alternatively, antisense-RNA is used to block translation of sense RNA. The antisense RNA is generated from a viral or plasmid DNA vector that contains a copy of the target gene situated in the reverse orientation with respect to the direction of transcription. A virus may be used as a carrier to introduce the inverted gene into the target cell genome. (Izant, J. G. and Weintmub H., Science 229:345–352(1985)).

Fragments of the anti-sense DNA segment are also provided herein and they may comprise about 15 to 100 bases, and more preferably 30 to 50 bases. The anti-sense sequences may be obtained by methods known in the art such as the following.

Antisense oligonucleotides can be made by modifying their phosphate moiety to increase biological lifetime, to enhance permeability into cells and to strengthen binding to target. For example, oligomethylphosphonates (Miller, P. S., Reddy, M. P., Murakami, A., Blake, K. R., Lin, S. B. and Agris, C. H. (1986) Biochemistry 25:5092–5097), or oligophosphorothionates (LaPlanche, L. A., James, T. L., Powell, C., Wilson, W. D., Uznanski, B., Stec., W. J., Summers, M. F. and Zon, G. (1986) Nucleic Acids Res. 14:9081–9093). Alternatively, the target gene may be inserted into a viral-based eukaryotic expression vector in reverse orientation and introduced into mammalian cells (See, Sambrook, J. et al, supra).

Also part of this invention is a pharmaceutical composition which comprises a therapeutically effective amount of an anti-sense DNA sequence to the coding strand of a polynucleotide encoding a polypeptide having the antibody binding specificity of the about 46 kDalton HMFG differentiation antigen or a fragment thereof; and a pharmaceutically acceptable carrier.

The composition may be provided in different amounts, Typically, the anti-sense DNA will be provided in an amount of about 0.01 to 99.99 wt % and more preferably about 0.1 to 20 wt %, the remainder being carrier and/or other known additives. The pharmaceutically acceptable carrier may be any carrier which does not degrade DNA. Examples of carriers and other additives are buffered saline solution, human serum albumin and the like. However, others may also be utilized. The pharmaceutical composition may be prepared by admixing the anti-sense DNA with the carrier as is known in the art, freeze dried and packaged in a sterile container. The composition may be maintained refrigerated and/or frozen.

A method of treating breast cancer in a subject in need of such treatment is provided with this invention. The method comprises administering to a subject a composition comprising a therapeutically effective amount of an anti-sense DNA sequence to the coding strand of a polynucleotide encoding a polypeptide having the antibody binding specificity of tile about 46 kDalton HMFG differentiation antigen or a fragment thereof.

This method may be practiced by administering an amount of about 5 to 800 mg anti-sense DNA, and more preferably about 20 to 200 mg anti-sense DNA in a pharmaceutical composition. The composition may be administered by a parenteral, intravenous or intrabreast route. However, other routes of administration may also be utilized.

Part of this invention is also an immunoassay kit comprising, in separate containers a monoclonal antibody having specificity for a polypeptide provided with the antibody binding activity of the about 46 kDalton HMFG differentiation antigen and/or homology to at least one of the light chains of clotting facters V and VIII; and anti-antibody immunoglobulin.

This immunoassay kit may be utilized for the practice of the various methods provided herein. The monoclonal antibody and the anti-antibody immunoglobulin may be provided in an amount of about 0.001 mg to 100 grams, and more preferably about 0.01 mg to 1 gram. The anti-antibody immunoglobulin may be a polyclonal immunoglobulin, protein A or protein G or functional fragments thereof, which may be labeled prior to use by methods known in the art.

Also provided herein is an antibody detecting kit comprising, in separate containers a polypeptide having the antibody binding specificity of the about 46 kDalton HMFG differentiation antigen and/or homology to at least one of the light chains of clotting factors V and VIII; and anti-antibody immunoglobulin.

The anti-antibody immunoglobulin may be labeled prior to use.

Also provided herein is a fusion protein kit comprising, in separate containers a fusion protein comprising a polypeptide provided with the antibody binding specificity of the about 46 kDalton HMFG differentiation antigen and/or homology to at least one of the light chains of clotting factors V and VIII and a second antigenic polypeptide or an antibody binding functional fragment thereof bound to one another;

an anti-second polypeptide monoclonal antibody; and anti-antibody immunoglobulin.

The fusion protein may be provided in an amount of about 0.001 mg to 100 grams in sterile form, and more preferably about 0.01 mg to 1 gram. The anti-second polypeptide monoclonal antibody may also be provided in sterile form in an amount of about 0.001 mg to 100 grams, and more preferably about 0.01 mg to 1 gram. The anti-antibody immunoglobulin may be provided in a separate container in an amount of about 0,001 mg to 100 grams and more preferably about 0.01 mg to 1 gram. The entire kit may be packaged for shipping and storage.

Also provided herein is an anti-breast cancer therapeutic kit comprising, in separate containers a monoclonal antibody having specificity for a polypeptide provided with the antibody binding specificity of the about 46 kDalton HMFG differentiation antigen and/or homology to at least one of the light chains of clotting factors V and VIII; and an anti-cancer therapeutic agent selected from the group consisting of immunotoxins and radionuclides.

The monoclonal antibody is provided in an amount of about 1 to 20 grams, and more preferably about 2 to 10 grams in sterile form. The antibody may be freeze-dried and packaged. The therapeutic agent may be any known anti-cancer therapeutic agent. By means of example the agent may be abrin-A chain, ricin A-chain, immunotoxins, chemotherapy drugs and 131I and 90 Y radionuclides, among others.

Having now generally described this invention, the same will be better understood by reference to certain specific examples, which are included herein for purposes of illustration only and are not intended to be limiting of the invention or any embodiment thereof, unless so specified.

EXAMPLES

Example 1: Immunoscreening lambda/gt11 cDNA library

A human breast cDNA library was purchased from Clontech (Palo Alto, Calif.). The library was prepared from RNA extracted from adult breast tissue excised during mastectomy, during 8th month pregnancy, showing well-differentiated tissue and lactational competence. The oligo-dT primed cDNA from this tissue was inserted into the Eco R1 site of lambda/gt11. Plating and screening of the library with MoAbs were done essentially as described by Young and Davis (Young, R. A. and Davis, R. W. (1983), Proc. Nat'l Acad. Sci. U.S.A., 80, 1194–1198). The library was screened with a cocktail of MoAbs Mc3, Mc8, Mc15 and Mc16 [Peterson, J. A. et al. Hybridoma 9:221–235, 1990 , all of which bind the 46 kDa component of human milk fat globule.

Example 2: Blot Analysis

Cell lines were grown to late log phase and total cell RNA prepared by the method of Chirgwin et al (Chirgwin, J. M., Przybyla, A. E., MacDonald, R. J., and Rutter, W. J. (1979) Biochemistry, 18, 5294–5299. RNA was glyoxalated, electrophoresed, and blotted according Thomas (Thomas, P. Hybridization of denatured RNA and small DNA fragments transferred to nitrocellulose. Proc. Nat'l. Acad. Sci. U.S.A., 77, 5201–5205) and RNA bound to nylon (Biodyne) filters using UV irradiation.

Single stranded RNA probes were made in vitro, using SP6 and T7 RNA polymerase according to manufacturer (Promega) and labelled by incorporation of [32P] UTP at 800 Ci/mmol (Amersham). Hybridization of RNA probes to RNA blots was at 70° C., 0.1×SSC, 0.1% SDS. Blots were exposed to X-ray film (Kodak X-AR) at −80° C. with intensifying screens.

Example 3: DNA Sequencing

Large scale bacteriophage DNA preparations were made from phage lysates, and the Eco R1 digested cDNA insert subcloned into pGEM3 (Promega, Madison, Wis.) according to standard protocols (Sambrook, J., Fritsch, D., and Maniatis, T. (1990) Molecular Cloning: A Laboratory Manual/Second edition, Cold Spring Harbor Laboratory Press, Cold Spring Harbor, N.Y.).

Dideoxy sequencing of the insert in pGEM3 was done with a modified T7 DNA polymerase (Sequenase) directly on the plasmid DNA using T7 or SP6 promoter sequence primers (Promega) according to the manufacturer's protocol (USB, Cleveland, Ohio). The sequence was confirmed by sequencing both strands of the insert.

Example 4: Results 15 positive plaques were selected after screening about 1×10$^6$ plaques from lambda/gt11 lactating breast cDNA library. The largest cDNA, BA46-1 was 1271 base pairs long. A second cDNA clone gave 3' end sequence data extending to 1384 base pairs, including the polyadenylation site. A series of positive lambda/gt11 clones were used to lysogenize Y1089 and the resulting fusion protein contained in induced cell extracts were analyzed by dot blot analysis for reactivity with each of the monoclonal Abs contained in the screening cocktail.

It was found that Mc8, Mc15 and Mc16 bound to all the positive lambda/gt11 lysogen extracts but not to control lambda/gt11 extract (not shown). Mc3, however, did not bind any of the lysates indicating that its epitope requires glycosylation, secondary structure, or is not present in the library.

Example 5: Study of RNA Sequence

Single stranded RNA probes representing each strand of the BA46-1 cDNA insert were prepared by subcloning into Gem3 and transcribing in vitro with T7 or SP6 polymerase.

Several carcinoma cell lines were studied including 5 breast lines and a lymphoid cell line for BA46-1 specific RNA. As shown in the figure accompanying this patent, a single 2.2 kb RNA was readily detected in most carcinoma cell lines tested. This RNA is also detectable in Raji, SKBR3 and PANC1, but at much lower levels requiring longer exposures than shown in the figure.

There was considerable variation in the observed expression levels of the 2.2 kb RNA that were detected in the carcinoma cell lines. The lung (A549), ovary (SKOV3) and two breast (E11-G and HS578T) cell lines accumulated from 10–50 fold more of this transcript than the other carcinoma cell lines. It should be noted that overexpression of certain genes, such as Her 2/neu and EGF receptor in breast and other carcinomas has previously been correlated with prognosis. (Slamon, D. J., Goldophin, W., Jones, L. A., Holt, J. A., Wong, S. G., Keith, D. E., Levin, W. J., Stuart, S. G., Udove, J., Ullrich, A., and Press, M. F. (1989) Science 244, 707–712.)(Dickson, R. B., Bates, S. E., McManaway, M. E., and Lippman, M. E. (1986) Cancer Res., 46, 1707–1713).

Example 6: Specificity Studies

Although the antibodies used to select the cDNA had specificity for breast carcinomas (Peterson, J. A., et al., Hybridoma 9:221–235 (1990)), expression of the about 2.2 kb RNA fragment that encodes the about 46 kDa protein occurs in many different carcinoma cell lines. A lack of breast specificity found may be attributed to a de-regulation of this gene in carcinomas but not in normal tissue. Alternatively, normal epithelial tissue may express the about 46 kDa protein but process it in a way that blocks the epitopes that are exposed in the breast cell version of the protein by, for example, alterations in glycosylation.

The high molecular weight mucin-like protein of HMFG is also expressed in non-breast carcinomas but its altered processing in the pancreas, for example, leads to exposure of different antigenic sites than in the breast (Lan, M. S., Hollingworth, M. A., and Metzgar, T. S. (1990) Cancer Res., 50, 2997–3001).

Example 7: Study of DNA Sequence

The nucleotide and derived amino acid composite sequence of Ba46 and Bu46-2 cDNAs is shown in Table 1 below.

TABLE 1

DNA Sequence and derived Amino Acid Sequence of BA46-1 cDNA

```
        *         10        *         20        *         30        *         40
GAT  TTC  ATC  CAT  GAT  GTT  AAT  AAA  AAA  CAC  AAG  GAG  TTT  GTG
Asp  Phe  Ile  His  Asp  Val  Asn  Lys  Lys  His  Lys  Glu  Phe  Val

*         50        *         60        *         70        *         80
GGT  AAC  TGG  AAC  AAA  AAC  GCG  GTG  CAT  GTC  AAC  CTC  TTT  GAG
Gly  Asn  Trp  Asn  Lys  Asn  Ala  Val  His  Val  Asn  Leu  Phe  Glu

*         90        *        100        *        110        *        120        *
ACC  CCT  GTG  GAG  GCT  CAG  TAC  GTG  AGA  TTG  TAC  CCC  ACG  AGC
Thr  Pro  Val  Glu  Ala  Gln  Tyr  Val  Arg  Leu  Tyr  Pro  Thr  Ser

130        *        140        *        150        *        160        *
TGC  CAC  ACG  GCC  TGC  ACT  CTG  CGC  TTT  GAG  CTA  CTG  GGC  TGT
Cys  His  Thr  Ala  Cys  Thr  Leu  Arg  Phe  Glu  Leu  Leu  Gly  Cys

170        *        180        *        190        *        200        *        210
GAG  CTG  AAC  GGA  TGC  GCC  AAT  CCC  CTG  GGC  CTG  AAG  AAT  AAC
Glu  Leu  Asn  Gly  Cys  Ala  Asn  Pro  Leu  Gly  Leu  Lys  Asn  Asn

*        220        *        230        *        240        *        250
AGC  ATC  CCT  GAC  AAG  CAG  ATC  ACG  GCC  TCC  AGC  AGC  TAC  AAG
Ser  Ile  Pro  Asp  Lys  Gln  Ile  Thr  Ala  Ser  Ser  Ser  Tyr  Lys

*        260        *        270        *        280        *        290
ACC  TGG  GGC  TTG  CAT  CTC  TTC  AGC  TGG  AAC  CCC  TCC  TAT  GCA
Thr  Trp  Gly  Leu  His  Leu  Phe  Ser  Trp  Asn  Pro  Ser  Tyr  Ala

*        300        *        310        *        320        *        330        *
CGG  CTG  GAC  AAG  CAG  GGC  AAC  TTC  AAC  GCC  TGG  GTT  GCG  GGG
Arg  Leu  Asp  Lys  Gln  Gly  Asn  Phe  Asn  Ala  Trp  Val  Ala  Gly
```

TABLE 1-continued

DNA Sequence and derived Amino Acid Sequence of BA46-1 cDNA

```
     340         *     350         *     360         *     370         *
AGC  TAC  GGT  AAC  GAT  CAG  TGG  CTG  CAG  GTG  GAC  CTG  GGC  TCC
Ser  Tyr  Gly  Asn  Asp  Gln  Trp  Leu  Gln  Val  Asp  Leu  Gly  Ser

380         *     390         *     400         *     410         *     420
TCG  AAG  GAG  GTG  ACA  GGC  ATC  ATC  ACC  CAG  GGG  GCC  CGT  AAC
Ser  Lys  Glu  Val  Thr  Gly  Ile  Ile  Thr  Gln  Gly  Ala  Arg  Asn

*     430         *     440         *     450         *     460
TTT  GGC  TCT  GTC  CAG  TTT  GTG  GCA  TCC  TAC  AAG  GTT  GCC  TAC
Phe  Gly  Ser  Val  Gln  Phe  Val  Ala  Ser  Tyr  Lys  Val  Ala  Tyr

*     470         *     480         *     490         *     500
AGT  AAT  GAC  AGT  GCG  AAC  TGG  ACT  GAG  TAC  CAG  GAC  CCC  AGG
Ser  Asn  Asp  Ser  Ala  Asn  Trp  Thr  Glu  Tyr  Gln  Asp  Pro  Arg

*     510         *     520         *     530         *     540         *
ACT  GGC  AGC  AGT  AAG  ATC  TTC  CCT  GGC  AAC  TGG  GAC  AAC  CAC
Thr  Gly  Ser  Ser  Lys  Ile  Phe  Pro  Gly  Asn  Trp  Asp  Asn  His

550         *     560         *     570         *     580         *
TCC  CAC  AAG  AAG  AAC  TTG  TTT  GAG  ACG  CCC  ATC  CTG  GCT  CGC
Ser  His  Lys  Lys  Asn  Leu  Phe  Glu  Thr  Pro  Ile  Leu  Ala  Arg

590         *     600         *     610         *     620         *     630
TAT  GTG  CGC  ATC  CTG  CCT  GTA  GCC  TGG  CAC  AAC  CGC  ATC  GCC
Tyr  Val  Arg  Ile  Leu  Pro  Val  Ala  Trp  His  Asn  Arg  Ile  Ala

*     640         *     650         *     660         *     670
CTG  CGC  CTG  GAG  CTG  CTG  GGC  TGT  TAG  TGG  CCA  CCT  GCC  ACC
Leu  Arg  Leu  Glu  Leu  Leu  Gly  Cys  ---  (■)

*     680         *     690         *     700         *     710
CCC  AGG  TCT  TCC  TGC  TTT  CCA  TGG  GCC  CGC  TGC  CTC  TTG  GCT

*     720         *     730         *     740         *     750         *
TCT  CAG  CCC  CTT  TAA  ATC  ACC  ATA  GGG  CTG  GGG  ACT  GGG  GAA

760         *     770         *     780         *     790         *
GGG  GAG  GGT  GTT  CAG  AGG  CAG  CAC  CAC  CAC  ACA  GTC  ACC  CCT

800         *     810         *     820         *     830         *     840
CCC  TCC  CTC  TTT  CCC  ACC  CTC  CAC  CTC  TCA  CGG  GCC  CTG  CCC

*     850         *     860         *     870         *     880
CAG  CCC  CTA  AGC  CCC  GTC  CCC  TAA  CCC  CCA  GTC  CTC  ACT  GTC

*     890         *     900         *     910         *     920
CTG  TTT  TCT  TAG  GCA  CTG  AGG  GAT  CTG  AGT  AGG  TCT  GGG  ATG

*     930         *     940         *     950         *     960         *
GAC  AGG  AAA  GGG  CAA  AGT  AGG  GCG  TGT  GGT  TTC  CCT  GCC  CCT

970         *     980         *     990         *    1000         *
GTC  CGG  ACC  GCC  GAT  CCC  AGG  TGC  GTG  TGT  CTC  TGT  CTC  TCC
```

TABLE 1-continued

DNA Sequence and derived Amino Acid Sequence of BA46-1 cDNA

```
     1010        *     1020        *     1030        *     1040        *     1050
TAG CCC CTC TCT CAC ACA TCA CAT TCC CAT GGT GGC CTC AAG

*     1060        *     1070        *     1080        *     1090
AAA GGC CCG GAA GCC CCA GGC TGG AGA TAA CAG CCT CTT GCC

*     1100        *     1110        *     1120        *     1130
CGT CGG CCC TGC GTC GGC CCT GGG GTA CCA TGT GCC ACA ACT

*     1140        *     1150        *     1160        *     1170        *
GCT GTG GCC CCC TGT CCC CAA GAC ACT TCC CCT TGT CTC CCT

1180        *     1190        *     1200        *     1210        *
GGT TGC CTC TCT TGC CCC TTG TCC TGA AGC CCA GCG ACA CAG

1220        *     1230        *     1240        *     1250        *     1260
AAG GGG GTG GGG CGG GTC TAT GGG GAG AAA GGG AGC GAG GTC

*     1270        *     1280        *     1290        *     1300
AGA GGA GGG CAT GGG TTG GCA GGG TGG GCG TTT GGG GCC CTC

*     1310        *     1320        *     1330        *     1340
ATG CTG GCT TTT CAC CCC AGA GGA CAC AGG CAG CTT CCA AAA

*     1350        *     1360        *     1370        *     1380
TAT ATTTAT CTT CTT CAC GGG AAA AAA AAA AAA AAA ACC G (□)
```

(□): SEQ. No. 1
(■): SEQ. No. 2

Potential n-linked glycosylation sites are underlined.

The partial sequence is 218 amino acids long and corresponds to a theoretical molecular weight of about 24 kDa, representing the C-terminus of the complete protein. There are 4 potential sites for n-linked glycosylation. The sequence is asparagine and leucine rich.

Example 8: Homology to Clotting Factors

A comparison of the nucleotide sequence to the EMBL database using FSTNSCAN (PCGENE) revealed extended homology with human serum factors V and VIII and protein C.

The derived protein sequence, however, shares identity only with factors V and VIII, as shown in Table 2 below, but not with protein C, since the homology at the nucleotide level is in an intervening sequence.

TABLE 2

Comparison of Derived BA46-1 Amino Acid Sequence with C-terminal Serum Factors V and VIII.

| 46 kDa | | | | F | I | H | D | V | N | K | K | H | K | E | F | V | G | N | W | N | K | N | A | V | H | V | N |
|---|---|---|---|---|---|---|---|---|---|---|---|---|---|---|---|---|---|---|---|---|---|---|---|---|---|---|---|
| FAV | | | | F | K | G | N | S | T | R | N | V | M | Y | F | N | G | N | S | D | A | S | T | I | K | E | N |
| FAVIII | | | | Y | R | G | N | S | T | G | T | L | M | V | F | F | G | N | V | D | S | S | G | I | K | H | N |
| L | F | E | T | P | V | E | A | Q | Y | V | R | L | Y | P | T | S | C | H | T | A | C | T | L | R | F | E | L |
| Q | F | D | P | P | I | V | A | R | Y | I | R | I | S | P | T | R | A | Y | N | R | P | T | L | R | L | E | L |
| I | F | N | P | P | I | I | A | R | Y | I | R | L | H | P | T | H | Y | S | I | R | S | T | L | R | M | E | L |
| L | G | C | E | L | N | G | C | A | N | P | L | G | L | K | N | N | S | I | P | D | K | Q | I | T | A | S | S |
| Q | G | C | E | V | N | G | C | S | T | P | L | G | M | E | N | G | K | I | E | N | K | Q | I | T | A | S | S |
| M | G | C | D | L | N | S | C | S | M | P | L | G | M | E | S | K | A | I | S | D | A | Q | I | T | A | S | S |
| S | Y | K | T | W | G | L | H | L | F | S | W | N | P | S | Y | A | R | L | D | K | Q | G | N | F | N | A | W |
| F | K | K | S | W | W | G | D | Y | — | — | W | E | P | F | R | A | R | L | N | A | Q | G | R | V | N | A | W |
| Y | F | T | N | M | F | A | T | — | — | — | W | S | P | S | K | A | R | L | H | L | Q | G | R | S | N | A | W |
| V | A | G | S | Y | G | N | D | Q | W | L | Q | V | D | L | G | S | S | K | E | V | T | G | I | I | T | Q | G |
| Q | A | K | A | N | N | N | K | Q | W | L | E | I | D | L | L | K | I | K | K | K | I | T | A | I | I | T | Q | G |
| R | P | Q | V | N | N | P | K | E | W | L | Q | V | D | F | Q | K | T | M | K | V | T | G | V | T | T | Q | G |
| A | R | N | F | G | S | V | Q | F | V | A | S | Y | K | V | A | Y | S | N | D | S | A | N | W | T | E | Y | Q |
| C | K | S | L | S | S | E | M | Y | V | K | S | Y | T | I | H | Y | S | E | Q | G | V | E | W | K | P | Y | R |
| V | K | S | L | L | T | E | M | Y | V | K | E | F | L | I | S | S | S | Q | D | G | H | Q | W | T | L | F | F |
| D | P | R | T | G | S | S | S | K | I | F | P | G | N | W | D | N | H | S | H | K | K | N | L | F | E | T | P | I |

TABLE 2-continued

Comparison of Derived BA46-1 Amino Acid Sequence with C-terminal Serum Factors V and VIII.

| L | K | S | S | M | V | D | K | I | F | E | G | N | T | N | T | K | G | H | V | K | N | F | F | N | P | P | I |
|---|---|---|---|---|---|---|---|---|---|---|---|---|---|---|---|---|---|---|---|---|---|---|---|---|---|---|---|
| Q | N | — | — | G | K | V | K | V | F | Q | G | N | Q | D | S | F | T | P | V | V | N | S | L | D | P | P | L |
| L | A | R | Y | V | R | I | L | P | V | A | W | H | N | R | I | A | L | R | L | E | L | L | G | C | | | |
| I | S | R | F | I | R | V | I | P | K | T | W | N | Q | S | I | A | L | R | L | E | L | F | G | C | D | — | — |
| L | T | R | Y | L | R | I | H | P | Q | S | W | V | H | Q | I | A | L | R | M | E | V | L | G | C | E | A | Q |
| (SEQ. No. 3) | | | | | | | | | | | | | | | | | | | | | | | | | | | |
| — | I | Y | (SEQ. No. 4) | | | | | | | | | | | | | | | | | | | | | | | | |
| D | L | Y | (SEQ. No. 5) | | | | | | | | | | | | | | | | | | | | | | | | |

An arrow indicates junction of C1 and C2 repeats.

There is about 43% identity of BA46 to Factor V and about 38% to factor VIII. The region of factors V and VIII in Table 2 share about 47% identity.

Example 9: Study of Amino Acid Sequence

The analysis of the derived amino acid sequence of the about 46 kDa protein is consistent with its description as a glycosylated protein. The function of this protein, however, is unknown. Since the about 46 kDa protein has homology to both factors V and VIII, there may be a common ancestral protein to these serum clotting factors. The homology is in the C1, C2 region of the light chain of factor VIII (Arai, M., Scandella, D., and Hoyer, L. W. (1989) J. Clin. Invest., 83, 1978–1984).

Arai et al have shown that human antibodies that bind this region of the light chain, from hemophiliacs treated with factor VIII, inhibit factor VIII by preventing the interaction of factor VIII with phospholipids. Since this region has been implicated in phospholipid binding it is likely that it serves a similar role in the about 46 kDa glycoprotein.

The C-terminal portion may thus serve as a novel "anchor" sequence for the 46 kDa protein or it may possibly be involved in the binding of the mucin/membrane to the phospholipids on the surface of the growing milk fat droplet (Long, C. A., and Patton, S. (1978(J. Dairy Sci., 61, 1392–1399). Perhaps, it is involved in the assembly of the mucin complex at the plasma membrane surface.

---

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 1384 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
GATTTCATCC  ATGATGTTAA  TAAAAAACAC  AAGGAGTTTG  TGGGTAACTG  GAACAAAAAC    60
GCGGTGCATG  TCAACCTGTT  TGAGACCCCT  GTGGAGGCTC  AGTACGTGAG  ATTGTACCCC   120
ACGAGCTGCC  ACACGGCCTG  CACTCTGCGC  TTTGAGCTAC  TGGGCTGTGA  GCTGAACGGA   180
TGCGCCAATC  CCCTGGGCCT  GAAGAATAAC  AGCATCCCTG  ACAAGCAGAT  CACGGCCTCC   240
AGCAGCTACA  AGACCTGGGG  CTTGCATCTC  TTCAGCTGGA  ACCCCTCCTA  TGCACGGCTG   300
GACAAGCAGG  GCAACTTCAA  CGCCTGGGTT  GCGGGGAGCT  ACGGTAACGA  TCAGTGGCTG   360
CAGGTGGACC  TGGGCTCCTC  GAAGGAGGTG  ACAGGCATCA  TCACCCAGGG  GGCCCGTAAC   420
TTTGGCTCTG  TCCAGTTTGT  GGCATCCTAC  AAGGTTGCCT  ACAGTAATGA  CAGTGCGAAC   480
TGGACTGAGT  ACCAGGACCC  CAGGACTGGC  AGCAGTAAGA  TCTTCCCTGG  CAACTGGGAC   540
AACCACTCCC  ACAAGAAGAA  CTTGTTTGAG  ACGCCCATCC  TGGCTCGCTA  TGTGCGCATC   600
CTGCCTGTAG  CCTGGCACAA  CCGCATCGCC  CTGCGCCTGG  AGCTGCTGGG  CTGTTAGTGG   660
CCACCTGCCA  CCCCCAGGTC  TTCCTGCTTT  CCATGGGCCC  GCTGCCTCTT  GGCTTCTCAG   720
```

```
CCCCTTTAAA  TCACCATAGG  GCTGGGGACT  GGGGAAGGGG  AGGGTGTTCA  GAGGCAGCAC   780
CACCACACAG  TCACCCCTCC  CTCCCTCTTT  CCCACCCTCC  ACCTCTCACG  GGCCCTGCCC   840
CAGCCCCTAA  GCCCCGTCCC  CTAACCCCCA  GTCCTCACTG  TCCTGTTTTC  TTAGGCACTG   900
AGGGATCTGA  GTAGGTCTGG  GATGGACAGG  AAAGGGCAAA  GTAGGGCGTG  TGGTTTCCCT   960
GCCCCTGTCC  GGACCGCCGA  TCCCAGGTGC  GTGTGTCTCT  GTCTCTCCTA  GCCCCTCTCT  1020
CACACATCAC  ATTCCCATGG  TGGCCTCAAG  AAAGGCCCGG  AAGCCCCAGG  CTGGAGATAA  1080
CAGCCTCTTG  CCCGTCGGCC  CTGCGTCGGC  CCTGGGGTAC  CATGTGCCAC  AACTGCTGTG  1140
GCCCCCTGTC  CCCAAGACAC  TTCCCCTTGT  CTCCCTGGTT  GCCTCTCTTG  CCCCTTGTCC  1200
TGAAGCCCAG  CGACACAGAA  GGGGGTGGGG  CGGGTCTATG  GGGAGAAAGG  GAGCGAGGTC  1260
AGAGGAGGGC  ATGGGTTGGC  AGGGTGGGCG  TTTGGGGCCC  TCATGCTGGC  TTTTCACCCC  1320
AGAGGACACA  GGCAGCTTCC  AAAATATATT  TATCTTCTTC  ACGGGAAAAA  AAAAAAAAA   1380
ACCG                                                                   1384
```

( 2 ) INFORMATION FOR SEQ ID NO:2:

( i ) SEQUENCE CHARACTERISTICS:
      ( A ) LENGTH: 218 amino acids
      ( B ) TYPE: amino acid
      ( C ) STRANDEDNESS: single
      ( D ) TOPOLOGY: linear ( i i ) MOLECULE TYPE: protein ( v ) FRAGMENT TYPE:

( x i ) SEQUENCE DESCRIPTION: SEQ ID NO:2:

```
Asp  Phe  Ile  His  Asp  Val  Asn  Lys  Lys  His  Lys  Glu  Phe  Val  Gly
  1              5                        10                       15

Asn  Trp  Asn  Lys  Asn  Ala  Val  His  Val  Asn  Leu  Phe  Glu  Thr  Pro
                20                       25                       30

Val  Glu  Ala  Gln  Tyr  Val  Arg  Leu  Tyr  Pro  Thr  Ser  Cys  His  Thr
                35                       40                       45

Ala  Cys  Thr  Leu  Arg  Phe  Glu  Leu  Leu  Gly  Cys  Glu  Leu  Asn  Gly
                50                       55                       60

Cys  Ala  Asn  Pro  Leu  Gly  Leu  Lys  Asn  Asn  Ser  Ile  Pro  Asp  Lys
                65                       70                       75

Gln  Ile  Thr  Ala  Ser  Ser  Ser  Tyr  Lys  Thr  Trp  Gly  Leu  His  Leu
                80                       85                       90

Phe  Ser  Trp  Asn  Pro  Ser  Tyr  Ala  Arg  Leu  Asp  Lys  Gln  Gly  Asn
                95                      100                      105

Phe  Asn  Ala  Trp  Val  Ala  Gly  Ser  Tyr  Gly  Asn  Asp  Gln  Trp  Leu
               110                      115                      120

Gln  Val  Asp  Leu  Gly  Ser  Ser  Lys  Glu  Val  Thr  Gly  Ile  Ile  Thr
               125                      130                      135

Gln  Gly  Ala  Arg  Asn  Phe  Gly  Ser  Val  Gln  Phe  Val  Ala  Ser  Tyr
               140                      145                      150

Lys  Val  Ala  Tyr  Ser  Asn  Asp  Ser  Ala  Asn  Trp  Thr  Glu  Tyr  Gln
               155                      160                      165

Asp  Pro  Arg  Thr  Gly  Ser  Ser  Lys  Ile  Phe  Pro  Gly  Asn  Trp  Asp
               170                      175                      180

Asn  His  Ser  His  Lys  Lys  Asn  Leu  Phe  Glu  Thr  Pro  Ile  Leu  Ala
               185                      190                      195
```

Arg Tyr Val Arg Ile Leu Pro Val Ala Trp His Asn Arg Ile Ala
                    200                 205                 210

Leu Arg Leu Glu Leu Leu Gly Cys
                215

(2) INFORMATION FOR SEQ ID NO:3:

(i) SEQUENCE CHARACTERISTICS:
        (A) LENGTH: 217 amino acids
        (B) TYPE: amino acid
        (C) STRANDEDNESS: single
        (D) TOPOLOGY: linear (ii) MOLECULE TYPE: protein (v) FRAGMENT TYPE:

(xi) SEQUENCE DESCRIPTION: SEQ ID NO:3:

Phe Ile His Asp Val Asn Lys Lys His Lys Glu Phe Val Gly Asn
1                5                   10                  15

Trp Asn Lys Asn Ala Val His Val Asn Leu Phe Glu Thr Pro Val
                20                  25                  30

Glu Ala Gln Tyr Val Arg Leu Tyr Pro Thr Ser Cys His Thr Ala
                35                  40                  45

Cys Thr Leu Arg Phe Glu Leu Leu Gly Cys Glu Leu Asn Gly Cys
                50                  55                  60

Ala Asn Pro Leu Gly Leu Lys Asn Asn Ser Ile Pro Asp Lys Gln
                65                  70                  75

Ile Thr Ala Ser Ser Ser Tyr Lys Thr Trp Gly Leu His Leu Phe
                80                  85                  90

Ser Trp Asn Pro Ser Tyr Ala Arg Leu Asp Lys Gln Gly Asn Phe
                95                  100                 105

Asn Ala Trp Val Ala Gly Ser Tyr Gly Asn Asp Gln Trp Leu Gln
                110                 115                 120

Val Asp Leu Gly Ser Ser Lys Glu Val Thr Gly Ile Ile Thr Gln
                125                 130                 135

Gly Ala Arg Asn Phe Gly Ser Val Gln Phe Val Ala Ser Tyr Lys
                140                 145                 150

Val Ala Tyr Ser Asn Asp Ser Ala Asn Trp Thr Glu Tyr Gln Asp
                155                 160                 165

Pro Arg Thr Gly Ser Ser Lys Ile Phe Pro Gly Asn Trp Asp Asn
                170                 175                 180

His Ser His Lys Lys Asn Leu Phe Glu Thr Pro Ile Leu Ala Arg
                185                 190                 195

Tyr Val Arg Ile Leu Pro Val Ala Trp His Asn Arg Ile Ala Leu
                200                 205                 210

Arg Leu Glu Leu Leu Gly Cys
                215

(2) INFORMATION FOR SEQ ID NO:4:

(i) SEQUENCE CHARACTERISTICS:
        (A) LENGTH: 218 amino acids
        (B) TYPE: amino acid
        (C) STRANDEDNESS: single
        (D) TOPOLOGY: linear (ii) MOLECULE TYPE: protein (v) FRAGMENT TYPE:

( x i ) SEQUENCE DESCRIPTION: SEQ ID NO:4:

| Phe | Lys | Gly | Asn | Ser | Thr | Arg | Asn | Val | Met | Tyr | Phe | Asn | Gly | Asn |
|---|---|---|---|---|---|---|---|---|---|---|---|---|---|---|
| 1 | | | | 5 | | | | | 10 | | | | | 15 |

| Ser | Asp | Ala | Ser | Thr | Ile | Lys | Glu | Asn | Gln | Phe | Asp | Pro | Pro | Ile |
|---|---|---|---|---|---|---|---|---|---|---|---|---|---|---|
| | | | | 20 | | | | | 25 | | | | | 30 |

| Val | Ala | Arg | Tyr | Ile | Arg | Ile | Ser | Pro | Thr | Arg | Ala | Tyr | Asn | Arg |
|---|---|---|---|---|---|---|---|---|---|---|---|---|---|---|
| | | | | 35 | | | | | 40 | | | | | 45 |

| Pro | Thr | Leu | Arg | Leu | Glu | Leu | Gln | Gly | Cys | Glu | Val | Asn | Gly | Cys |
|---|---|---|---|---|---|---|---|---|---|---|---|---|---|---|
| | | | | 50 | | | | | 55 | | | | | 60 |

| Ser | Thr | Pro | Leu | Gly | Met | Glu | Asn | Gly | Lys | Ile | Glu | Asn | Lys | Gln |
|---|---|---|---|---|---|---|---|---|---|---|---|---|---|---|
| | | | | 65 | | | | | 70 | | | | | 75 |

| Ile | Thr | Ala | Ser | Ser | Phe | Lys | Lys | Ser | Trp | Trp | Gly | Asp | Tyr | Trp |
|---|---|---|---|---|---|---|---|---|---|---|---|---|---|---|
| | | | | 80 | | | | | 85 | | | | | 90 |

| Glu | Pro | Phe | Arg | Ala | Arg | Leu | Asn | Ala | Gln | Gly | Arg | Val | Asn | Ala |
|---|---|---|---|---|---|---|---|---|---|---|---|---|---|---|
| | | | | 95 | | | | | 100 | | | | | 105 |

| Trp | Gln | Ala | Lys | Ala | Asn | Asn | Asn | Lys | Gln | Trp | Leu | Glu | Ile | Asp |
|---|---|---|---|---|---|---|---|---|---|---|---|---|---|---|
| | | | | 110 | | | | | 115 | | | | | 120 |

| Leu | Leu | Lys | Ile | Lys | Lys | Ile | Thr | Ala | Ile | Ile | Thr | Gln | Gly | Cys |
|---|---|---|---|---|---|---|---|---|---|---|---|---|---|---|
| | | | | 125 | | | | | 130 | | | | | 135 |

| Lys | Ser | Leu | Ser | Ser | Glu | Met | Tyr | Val | Lys | Ser | Tyr | Thr | Ile | His |
|---|---|---|---|---|---|---|---|---|---|---|---|---|---|---|
| | | | | 140 | | | | | 145 | | | | | 150 |

| Tyr | Ser | Glu | Gln | Gly | Val | Glu | Trp | Lys | Pro | Tyr | Arg | Leu | Lys | Ser |
|---|---|---|---|---|---|---|---|---|---|---|---|---|---|---|
| | | | | 155 | | | | | 160 | | | | | 165 |

| Ser | Met | Val | Asp | Lys | Ile | Phe | Glu | Gly | Asn | Thr | Asn | Thr | Lys | Gly |
|---|---|---|---|---|---|---|---|---|---|---|---|---|---|---|
| | | | | 170 | | | | | 175 | | | | | 180 |

| His | Val | Lys | Asn | Phe | Phe | Asn | Pro | Pro | Ile | Ile | Ser | Arg | Phe | Ile |
|---|---|---|---|---|---|---|---|---|---|---|---|---|---|---|
| | | | | 185 | | | | | 190 | | | | | 195 |

| Arg | Val | Ile | Pro | Lys | Thr | Trp | Asn | Gln | Ser | Ile | Ala | Leu | Arg | Leu |
|---|---|---|---|---|---|---|---|---|---|---|---|---|---|---|
| | | | | 200 | | | | | 205 | | | | | 210 |

| Glu | Leu | Phe | Gly | Cys | Asp | Ile | Tyr |
|---|---|---|---|---|---|---|---|
| | | | | 215 | | | |

( 2 ) INFORMATION FOR SEQ ID NO:5:

( i ) SEQUENCE CHARACTERISTICS:
        ( A ) LENGTH: 218 amino acids
        ( B ) TYPE: amino acid
        ( C ) STRANDEDNESS: single
        ( D ) TOPOLOGY: linear ( i i ) MOLECULE TYPE: protein ( i i i ) FRAGMENT TYPE:

( x i ) SEQUENCE DESCRIPTION: SEQ ID NO:5:

| Tyr | Arg | Gly | Asn | Ser | Thr | Gly | Thr | Leu | Met | Val | Phe | Phe | Gly | Asn |
|---|---|---|---|---|---|---|---|---|---|---|---|---|---|---|
| 1 | | | | 5 | | | | | 10 | | | | | 15 |

| Val | Asp | Ser | Ser | Gly | Ile | Lys | His | Asn | Ile | Phe | Asn | Pro | Pro | Ile |
|---|---|---|---|---|---|---|---|---|---|---|---|---|---|---|
| | | | | 20 | | | | | 25 | | | | | 30 |

| Ile | Ala | Arg | Tyr | Ile | Arg | Leu | His | Pro | Thr | His | Tyr | Ser | Ile | Arg |
|---|---|---|---|---|---|---|---|---|---|---|---|---|---|---|
| | | | | 35 | | | | | 40 | | | | | 45 |

| Ser | Thr | Leu | Arg | Met | Glu | Leu | Met | Gly | Cys | Asp | Leu | Asn | Ser | Cys |
|---|---|---|---|---|---|---|---|---|---|---|---|---|---|---|
| | | | | 50 | | | | | 55 | | | | | 60 |

| Ser | Met | Pro | Leu | Gly | Met | Glu | Ser | Lys | Ala | Ile | Ser | Asp | Ala | Gln |
|---|---|---|---|---|---|---|---|---|---|---|---|---|---|---|
| | | | | 65 | | | | | 70 | | | | | 75 |

| Ile | Thr | Ala | Ser | Ser | Tyr | Phe | Thr | Asn | Met | Phe | Ala | Thr | Trp | Ser |
|---|---|---|---|---|---|---|---|---|---|---|---|---|---|---|
| | | | | 80 | | | | | 85 | | | | | 90 |

| | | | | | | | | | | | | | | |
|---|---|---|---|---|---|---|---|---|---|---|---|---|---|---|
| Pro | Ser | Lys | Ala | Arg 95 | Leu | His | Leu | Gln | Gly 100 | Arg | Ser | Asn | Ala | Trp 105 |
| Arg | Pro | Gln | Val | Asn 110 | Asn | Pro | Lys | Glu | Trp 115 | Leu | Gln | Val | Asp | Phe 120 |
| Gln | Lys | Thr | Met | Lys 125 | Val | Thr | Gly | Val | Thr 130 | Thr | Gln | Gly | Val | Lys 135 |
| Ser | Leu | Leu | Thr | Glu 140 | Met | Tyr | Val | Lys | Glu 145 | Phe | Leu | Ile | Ser | Ser 150 |
| Ser | Gln | Asp | Gly | His 155 | Gln | Trp | Thr | Leu | Phe 160 | Phe | Gln | Asn | Gly | Lys 165 |
| Val | Lys | Val | Phe | Gln 170 | Gly | Asn | Gln | Asp | Ser 175 | Phe | Thr | Pro | Val | Val 180 |
| Asn | Ser | Leu | Asp | Pro 185 | Pro | Leu | Leu | Thr | Arg 190 | Tyr | Leu | Arg | Ile | His 195 |
| Pro | Gln | Ser | Trp | Val 200 | His | Gln | Ile | Ala | Leu 205 | Arg | Met | Glu | Val | Leu 210 |
| Gly | Cys | Glu | Ala | Gln 215 | Asp | Leu | Tyr | | | | | | | |

The invention now being fully described, it will be apparent to one of ordinary skill in the art that many changes and modifications can be made thereto without departing from the spirit or scope of the invention as set forth herein.

We claim:

1. A purified, isolated polypeptide having the antibody binding specificity of the about 46 Kdalton human milk fat globule (HMFG) differentiation antigen.

2. The polypeptide of claim 1, being the about 46 Kdalton HMFG differentiation antigen or an antibody binding 218 amino acids long fragment thereof.

3. A composition, comprising an antibody binding effective amount of the polypeptide of claim 1, and a pharmaceutically acceptable carrier.

4. A method of detecting the presence in a biological sample of an antibody having affinity for the about 46 Kdalton human milk fat globule (HMFG) differentiation antigen, comprising obtaining a sample suspected of comprising the antibody;

adding thereto an antibody binding effective amount of the polypeptide of claim 1 under conditions effective to form an antibody-polypeptide complex; and determining the presence of any complex formed.

5. An antibody detecting kit comprising, in separate containers the polypeptide of claim 1; and anti-antibody immunoglobulin.

6. The polypeptide of claim 1, comprising at least one peptide fragment having sequence similarity to at least a portion of the C1 or C2 domains of clotting factor V or VIII.

* * * * *

UNITED STATES PATENT AND TRADEMARK OFFICE
CERTIFICATE OF CORRECTION

PATENT NO.   : 5,455,031
DATED        : October 3, 1995
INVENTOR(S)  : Roberto L. Ceriani et al.

It is certified that error appears in the above-identified patent and that said Letters Patent is hereby corrected as shown below:

On the title page: Item [56]

First column, Cover Page, Other Publications, Ceriani, R.L. et al., line 10, change "MOnoclonal" into --Monoclonal--.

First column, Cover page, Other Publications, Ceriani, R.L. et al., line 13, after "Human" change "Mannary" to read --Mammary--.

Second column, Cover page, Other Publications, Ceriani, R.L., et al., line 2, change "Circulsation" into --Circulation--.

Second column, Cover page, Other Publications, Ceriani, R.L., et al., line 3, change "Blobule" into --Globule--.

Second Column, Cover Page, Other Publications, Peterson, J.A., et al., line 12, after "vol" change "19" to --9--; and after "No. 3:" change (199) to --(1990)--.

Second Column, Cover Page, Other Publications, Ceriani, R.L., et al., line 13, change "mannary" into --mammary--.

UNITED STATES PATENT AND TRADEMARK OFFICE
CERTIFICATE OF CORRECTION

PATENT NO.    : 5,455,031
DATED         : October 3, 1995
INVENTOR(S)   : Roberto L. Ceriani et al.

It is certified that error appears in the above-identified patent and that said Letters Patent is hereby corrected as shown below:

Second column, Cover page, Other Publications, Ceriani, R.L., et al., line 2, change "breat" into --breast--.

Column 1, line 49 after "to" change "lave" into --have--.

Column 1, line 56, before "breast" change "kgtll" into --lambda/gt11--.

Column 9, line 46, after "has" change "tile" into --the--.

Column 10, line 3, delete --,-- after "human".

Column 11, line 17, change "10-10" into --$10^{-10}$--.

Column 11, line 17, change "10-5" into --$10^{-5}$--.

Column 11, line 18, change "tile" into --the--.

Column 11, line 37, change "tile" into --the--.

Column 12, line 28, change "laving" into --having--.

UNITED STATES PATENT AND TRADEMARK OFFICE
CERTIFICATE OF CORRECTION

PATENT NO.  : 5,455,031
DATED       : October 3, 1995
INVENTOR(S) : Roberto L. Ceriani et al.

It is certified that error appears in the above-identified patent and that said Letters Patent is hereby corrected as shown below:

Column 24, line 28, change "Ba46and Bu46-2" into --BA46-1 and BA46-2--.

Columns 23 & 24, Table 1, 2nd sequence, #78, change "C" into --G--.

Column 27, line 42, after "for" change "n-linked" into --N-linked--.

Signed and Sealed this

Twenty-fourth Day of June, 1997

Attest:

BRUCE LEHMAN

*Attesting Officer*     *Commissioner of Patents and Trademarks*